(12) United States Patent
Sathaye et al.

(10) Patent No.: US 8,527,048 B2
(45) Date of Patent: Sep. 3, 2013

(54) LOCAL AND NON-LOCAL SENSING FOR CARDIAC PACING

(75) Inventors: Alok S. Sathaye, Minneapolis, MN (US); Aaron R. McCabe, Minneapolis, MN (US); Yinghong Yu, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1229 days.

(21) Appl. No.: 11/478,286

(22) Filed: Jun. 29, 2006

(65) Prior Publication Data

US 2008/0009909 A1    Jan. 10, 2008

(51) Int. Cl.
*A61N 1/365* (2006.01)

(52) U.S. Cl.
USPC .......................................................... 607/17

(58) Field of Classification Search
USPC ............................................................ 607/9
See application file for complete search history.

(56) References Cited

U.S. PATENT DOCUMENTS

| | | |
|---|---|---|
| 3,920,005 A | 11/1975 | Gombrich et al. |
| 4,388,927 A | 6/1983 | Schober |
| 4,550,221 A | 10/1985 | Mabusth |
| 4,562,841 A | 1/1986 | Brockway et al. |
| 4,686,332 A | 8/1987 | Greanias et al. |
| 4,878,497 A | 11/1989 | Callaghan et al. |
| 4,928,688 A | 5/1990 | Mower |
| 4,953,551 A | 9/1990 | Mehra et al. |
| 5,036,849 A | 8/1991 | Hauck et al. |
| 5,133,353 A | 7/1992 | Hauser |
| 5,170,784 A | 12/1992 | Ramon et al. |
| 5,179,945 A | 1/1993 | Van Hofwegen et al. |
| 5,203,348 A | 4/1993 | Dahl et al. |
| 5,209,229 A | 5/1993 | Gilli |
| 5,222,493 A | 6/1993 | Sholder |
| 5,224,486 A | 7/1993 | Lerman et al. |

(Continued)

FOREIGN PATENT DOCUMENTS

| | | |
|---|---|---|
| EP | 0468720 | 1/1992 |
| EP | 0560569 | 9/1993 |

(Continued)

OTHER PUBLICATIONS

U.S. Appl. No. 11/209,976, filed Aug. 23, 2005, Li et al.

(Continued)

*Primary Examiner* — Carl H Layno
*Assistant Examiner* — Luther Behringer
(74) *Attorney, Agent, or Firm* — Brooks, Cameron & Huebsch, PLLC

(57) ABSTRACT

Systems and methods for determining pacing timing intervals based on the temporal relationship between the timing of local and non-local cardiac signal features are described. A device includes a plurality of implantable electrodes electrically coupled to the heart and configured to sense local and non-local cardiac signals. Sense circuitry coupled to first and second electrode pairs senses a local cardiac signal via a first electrode pair and a non-local cardiac signal via a second electrode pair. Detection circuitry is used to detect a feature of the local signal associated with activation of a heart chamber and to detect a feature of the non-local signal associated with activation of the heart chamber. A control processor times delivery of one or more pacing pulses based on a temporal relationship between timing of the local signal feature and timing of the non-local signal feature.

21 Claims, 10 Drawing Sheets

(56) References Cited

U.S. PATENT DOCUMENTS

| | | |
|---|---|---|
| 5,230,337 A | 7/1993 | Dahl et al. |
| 5,231,990 A * | 8/1993 | Gauglitz ................. 600/510 |
| 5,261,400 A | 11/1993 | Bardy |
| 5,271,411 A | 12/1993 | Ripley et al. |
| 5,284,136 A | 2/1994 | Hauck et al. |
| 5,292,338 A | 3/1994 | Bardy |
| 5,299,118 A | 3/1994 | Martens et al. |
| 5,300,106 A | 4/1994 | Dahl et al. |
| 5,301,677 A | 4/1994 | Hsung |
| 5,312,445 A * | 5/1994 | Nappholz et al. .................. 607/9 |
| 5,313,953 A | 5/1994 | Yomtov et al. |
| 5,314,430 A | 5/1994 | Bardy |
| 5,314,459 A | 5/1994 | Swanson et al. |
| 5,318,597 A | 6/1994 | Hauck et al. |
| 5,324,310 A | 6/1994 | Greeninger et al. |
| 5,331,966 A * | 7/1994 | Bennett et al. ................ 600/508 |
| 5,331,996 A | 7/1994 | Ziehm |
| 5,333,095 A | 7/1994 | Stevenson et al. |
| 5,334,222 A | 8/1994 | Salo et al. |
| 5,342,402 A | 8/1994 | Olson et al. |
| 5,350,410 A | 9/1994 | Kleks et al. |
| 5,360,442 A | 11/1994 | Dahl et al. |
| 5,366,496 A | 11/1994 | Dahl et al. |
| 5,372,606 A | 12/1994 | Lang et al. |
| 5,376,106 A | 12/1994 | Stahmann et al. |
| 5,388,578 A | 2/1995 | Yomtov et al. |
| 5,391,200 A | 2/1995 | KenKnight et al. |
| 5,397,342 A | 3/1995 | Heil, Jr. et al. |
| 5,411,031 A | 5/1995 | Yomtov |
| 5,411,525 A | 5/1995 | Swanson et al. |
| 5,411,533 A | 5/1995 | Dubreuil |
| 5,411,539 A | 5/1995 | Neisz |
| 5,431,693 A | 7/1995 | Schroeppel |
| 5,439,482 A | 8/1995 | Adams et al. |
| 5,441,518 A | 8/1995 | Adams et al. |
| 5,443,485 A | 8/1995 | Housworth et al. |
| 5,468,254 A | 11/1995 | Hahn et al. |
| 5,520,191 A | 5/1996 | Karlsson et al. |
| 5,531,779 A | 7/1996 | Dahl et al. |
| 5,540,727 A | 7/1996 | Tockman et al. |
| 5,545,186 A | 8/1996 | Olson et al. |
| 5,545,202 A | 8/1996 | Dahl et al. |
| 5,603,732 A | 2/1997 | Dahl et al. |
| 5,605,158 A | 2/1997 | Snell |
| 5,620,466 A | 4/1997 | Haefner et al. |
| 5,626,620 A | 5/1997 | Kieval et al. |
| 5,634,938 A | 6/1997 | Swanson et al. |
| 5,641,326 A | 6/1997 | Adams |
| 5,650,759 A | 7/1997 | Hittman et al. |
| 5,662,688 A | 9/1997 | Haefner et al. |
| 5,674,254 A | 10/1997 | van Krieken |
| 5,683,431 A | 11/1997 | Wang |
| 5,683,434 A | 11/1997 | Archer |
| 5,697,953 A | 12/1997 | Kroll et al. |
| 5,697,959 A | 12/1997 | Poore |
| 5,704,365 A | 1/1998 | Albrecht et al. |
| 5,724,984 A | 3/1998 | Arnold et al. |
| 5,735,882 A * | 4/1998 | Rottenberg et al. .............. 607/27 |
| 5,779,645 A | 7/1998 | Olson et al. |
| 5,803,084 A | 9/1998 | Olson |
| 5,827,326 A | 10/1998 | Kroll et al. |
| 5,836,987 A | 11/1998 | Baumann et al. |
| 5,844,506 A | 12/1998 | Binstead |
| 5,855,593 A | 1/1999 | Olson et al. |
| 5,861,013 A | 1/1999 | Peck et al. |
| 5,871,512 A | 2/1999 | Hemming et al. |
| 5,873,898 A | 2/1999 | Hemming et al. |
| 5,895,414 A | 4/1999 | Sanchez-Zambrano |
| 5,916,243 A | 6/1999 | KenKnight et al. |
| 5,957,956 A | 9/1999 | Kroll et al. |
| 5,983,138 A | 11/1999 | Kramer |
| 5,987,352 A | 11/1999 | Klein et al. |
| 6,026,320 A | 2/2000 | Carlson et al. |
| 6,038,474 A | 3/2000 | Zhu et al. |
| 6,044,298 A | 3/2000 | Salo et al. |
| 6,049,730 A | 4/2000 | Kristbjarmarson |
| 6,055,454 A | 4/2000 | Heemels |
| 6,101,416 A | 8/2000 | Sloman |
| 6,115,628 A | 9/2000 | Stadler et al. |
| 6,128,535 A | 10/2000 | Maarse |
| 6,134,473 A | 10/2000 | Hemming et al. |
| 6,141,581 A | 10/2000 | Olson et al. |
| 6,144,880 A | 11/2000 | Ding |
| 6,147,680 A | 11/2000 | Tareev |
| 6,148,230 A | 11/2000 | KenKnight |
| 6,148,234 A | 11/2000 | Struble |
| 6,163,724 A | 12/2000 | Hemming et al. |
| 6,169,921 B1 | 1/2001 | KenKnight et al. |
| 6,175,766 B1 | 1/2001 | Bornzin et al. |
| 6,192,275 B1 | 2/2001 | Zhu et al. |
| 6,221,011 B1 | 4/2001 | Bardy |
| 6,226,551 B1 | 5/2001 | Zhu et al. |
| 6,227,072 B1 | 5/2001 | Ritchey et al. |
| 6,238,419 B1 | 5/2001 | Lindgren |
| 6,253,102 B1 | 6/2001 | Hsu et al. |
| 6,259,947 B1 | 7/2001 | Olson et al. |
| 6,266,554 B1 | 7/2001 | Hsu et al. |
| 6,267,778 B1 * | 7/2001 | Cohen ............................. 607/9 |
| 6,270,457 B1 | 8/2001 | Bardy |
| 6,275,731 B1 | 8/2001 | Zhu et al. |
| 6,280,380 B1 | 8/2001 | Bardy |
| 6,280,462 B1 | 8/2001 | Hauser et al. |
| 6,282,440 B1 | 8/2001 | Brodnick et al. |
| 6,285,907 B1 | 9/2001 | Kramer et al. |
| 6,301,503 B1 | 10/2001 | Hsu et al. |
| 6,312,378 B1 | 11/2001 | Bardy |
| 6,324,421 B1 | 11/2001 | Stadler et al. |
| 6,324,427 B1 | 11/2001 | Florio |
| 6,336,903 B1 | 1/2002 | Bardy |
| 6,345,201 B1 | 2/2002 | Sloman et al. |
| 6,351,673 B1 | 2/2002 | Ding et al. |
| 6,358,203 B2 | 3/2002 | Bardy |
| 6,360,127 B1 | 3/2002 | Ding et al. |
| 6,368,284 B1 | 4/2002 | Bardy |
| 6,371,922 B1 | 4/2002 | Baumann et al. |
| 6,393,316 B1 | 5/2002 | Gillberg et al. |
| 6,398,728 B1 | 6/2002 | Bardy |
| 6,409,675 B1 | 6/2002 | Turcott |
| 6,411,848 B2 | 6/2002 | Kramer et al. |
| 6,415,174 B1 | 7/2002 | Bebehani et al. |
| 6,418,340 B1 | 7/2002 | Conley et al. |
| 6,424,234 B1 | 7/2002 | Stevenson |
| 6,424,865 B1 | 7/2002 | Ding |
| 6,434,428 B1 | 8/2002 | Sloman et al. |
| 6,438,409 B1 | 8/2002 | Malik et al. |
| 6,438,410 B2 | 8/2002 | Hsu et al. |
| 6,440,066 B1 | 8/2002 | Bardy |
| 6,449,503 B1 | 9/2002 | Hsu |
| 6,456,481 B1 | 9/2002 | Stevenson |
| 6,456,880 B1 | 9/2002 | Park et al. |
| 6,456,881 B1 | 9/2002 | Bornzin et al. |
| 6,459,929 B1 | 10/2002 | Hopper et al. |
| 6,466,820 B1 | 10/2002 | Juran et al. |
| 6,477,422 B1 | 11/2002 | Splett |
| 6,480,733 B1 | 11/2002 | Turcott |
| 6,487,443 B2 | 11/2002 | Olson et al. |
| 6,491,639 B1 | 12/2002 | Turcott |
| 6,496,715 B1 | 12/2002 | Lee et al. |
| 6,505,067 B1 | 1/2003 | Lee et al. |
| 6,505,071 B1 | 1/2003 | Zhu et al. |
| 6,512,940 B1 | 1/2003 | Brabec et al. |
| 6,512,953 B2 | 1/2003 | Florio et al. |
| 6,522,915 B1 | 2/2003 | Ceballos et al. |
| 6,542,775 B2 | 4/2003 | Ding et al. |
| 6,564,106 B2 | 5/2003 | Guck et al. |
| 6,567,701 B2 | 5/2003 | Vonk |
| 6,597,951 B2 | 7/2003 | Kramer et al. |
| 6,607,509 B2 | 8/2003 | Bobroff et al. |
| 6,609,027 B2 | 8/2003 | Kroll et al. |
| 6,615,082 B1 | 9/2003 | Mandell |
| 6,615,083 B2 | 9/2003 | Kupper |
| 6,618,619 B1 | 9/2003 | Florio et al. |
| 6,622,046 B2 | 9/2003 | Fraley et al. |
| 6,625,490 B1 | 9/2003 | McClure et al. |

| | | | | | |
|---|---|---|---|---|---|
| 6,631,290 B1 | 10/2003 | Guck et al. | 7,146,212 B2 | 12/2006 | Bardy et al. |
| 6,654,637 B2 | 11/2003 | Rouw et al. | 7,149,575 B2 | 12/2006 | Ostroff et al. |
| 6,658,293 B2 | 12/2003 | Vonk | 7,158,830 B2 | 1/2007 | Yu |
| 6,690,967 B2 | 2/2004 | Meij | 7,177,689 B2 | 2/2007 | Ternes et al. |
| 6,701,170 B2 | 3/2004 | Stetson | 7,181,285 B2 | 2/2007 | Lindh |
| 6,708,058 B2 | 3/2004 | Kim et al. | 7,184,835 B2 | 2/2007 | Kramer et al. |
| 6,725,085 B2 | 4/2004 | Schwartzmann et al. | 7,191,003 B2 | 3/2007 | Greenhut et al. |
| 6,738,669 B1 | 5/2004 | Sloman et al. | 7,191,004 B2 | 3/2007 | Kim et al. |
| 6,754,523 B2 | 6/2004 | Toole | 7,194,302 B2 | 3/2007 | Bardy et al. |
| 6,754,528 B2 | 6/2004 | Bardy et al. | 7,194,309 B2 | 3/2007 | Ostroff et al. |
| 6,760,615 B2 | 7/2004 | Ferek-Petric | 7,203,540 B2 | 4/2007 | Ding et al. |
| 6,766,190 B2 | 7/2004 | Ferek-Petric | 7,203,542 B2 | 4/2007 | Obel |
| 6,768,923 B2 | 7/2004 | Ding et al. | 7,203,543 B2 | 4/2007 | Meyer et al. |
| 6,768,924 B2 | 7/2004 | Ding et al. | 7,212,862 B2 | 5/2007 | Park et al |
| 6,778,860 B2 | 8/2004 | Ostroff et al. | 7,225,021 B1 | 5/2007 | Park et al. |
| 6,788,974 B2 | 9/2004 | Bardy et al. | 7,228,173 B2 | 6/2007 | Cazares |
| 6,834,204 B2 | 12/2004 | Ostroff et al. | 7,228,174 B2 | 6/2007 | Burnes |
| 6,856,835 B2 | 2/2005 | Bardy et al. | 7,236,819 B2 | 6/2007 | Brockway |
| 6,865,417 B2 | 3/2005 | Rissmann et al. | 7,242,978 B2 | 7/2007 | Cao |
| 6,866,044 B2 | 3/2005 | Bardy et al. | 7,245,962 B2 | 7/2007 | Ciaccio et al. |
| 6,871,096 B2 | 3/2005 | Hill | 7,248,925 B2 | 7/2007 | Bruhns et al. |
| 6,881,192 B1 | 4/2005 | Park | 7,263,399 B2 | 8/2007 | Carlson |
| 6,884,218 B2 | 4/2005 | Olson et al. | 7,277,754 B2 | 10/2007 | McCabe et al. |
| 6,885,893 B1 | 4/2005 | Lu | 7,286,876 B2 | 10/2007 | Yonce et al. |
| 6,888,538 B2 | 5/2005 | Ely et al. | 7,299,086 B2 | 11/2007 | McCabe et al. |
| 6,889,079 B2 | 5/2005 | Bocek et al. | 7,310,554 B2 | 12/2007 | Kramer |
| 6,895,274 B2 | 5/2005 | Mower | 7,319,900 B2 | 1/2008 | Kim et al. |
| 6,904,315 B2 | 6/2005 | Panken et al. | 7,359,749 B2 | 4/2008 | Quenet et al. |
| 6,925,324 B2 | 8/2005 | Shusterman | 7,457,664 B2 | 11/2008 | Zhang et al. |
| 6,925,330 B2 | 8/2005 | Kleine | 7,477,932 B2 | 1/2009 | Lee |
| 6,927,721 B2 | 8/2005 | Ostroff | 7,509,170 B2 | 3/2009 | Zhang et al. |
| 6,937,907 B2 | 8/2005 | Bardy et al. | 7,558,628 B2 | 7/2009 | Yonce et al. |
| 6,944,495 B2 | 9/2005 | MacAdam et al. | 7,580,741 B2 | 8/2009 | Cazares et al. |
| 6,944,579 B2 | 9/2005 | Shimizu | 7,653,431 B2 | 1/2010 | Cazares et al. |
| 6,950,702 B2 | 9/2005 | Sweeney | 7,818,056 B2 | 10/2010 | Kim et al. |
| 6,950,705 B2 | 9/2005 | Bardy et al. | 2002/0035334 A1 | 3/2002 | Meij et al. |
| 6,952,608 B2 | 10/2005 | Ostroff | 2002/0035376 A1 | 3/2002 | Bardy et al. |
| 6,952,610 B2 | 10/2005 | Ostroff | 2002/0035377 A1 | 3/2002 | Bardy et al. |
| 6,954,670 B2 | 10/2005 | Ostroff | 2002/0035378 A1 | 3/2002 | Bardy et al. |
| 6,959,214 B2 | 10/2005 | Pape et al. | 2002/0035379 A1 | 3/2002 | Bardy et al. |
| 6,961,613 B2 | 11/2005 | Bjorling et al. | 2002/0035380 A1 | 3/2002 | Rissmann et al. |
| 6,961,619 B2 | 11/2005 | Casey | 2002/0035381 A1 | 3/2002 | Bardy et al. |
| 6,973,350 B1 | 12/2005 | Levine et al. | 2002/0042629 A1 | 4/2002 | Bardy et al. |
| 6,975,904 B1 | 12/2005 | Sloman | 2002/0042630 A1 | 4/2002 | Bardy et al. |
| 6,983,264 B2 | 1/2006 | Shimizu | 2002/0042634 A1 | 4/2002 | Bardy et al. |
| 6,988,003 B2 | 1/2006 | Bardy et al. | 2002/0049475 A1 | 4/2002 | Bardy et al. |
| 6,993,379 B1 | 1/2006 | Kroll | 2002/0049476 A1 | 4/2002 | Bardy et al. |
| 6,993,389 B2 | 1/2006 | Ding | 2002/0052636 A1 | 5/2002 | Bardy et al. |
| 6,999,817 B2 | 2/2006 | Park et al. | 2002/0068958 A1 | 6/2002 | Bardy et al. |
| 7,006,869 B2 | 2/2006 | Bradley | 2002/0072773 A1 | 6/2002 | Bardy et al. |
| 7,027,861 B2 | 4/2006 | Thompson | 2002/0082658 A1 | 6/2002 | Heinrich et al. |
| 7,027,868 B2 | 4/2006 | Rueter et al. | 2002/0085741 A1 | 7/2002 | Shimizu |
| 7,039,459 B2 | 5/2006 | Bardy | 2002/0091414 A1 | 7/2002 | Bardy et al. |
| 7,039,465 B2 | 5/2006 | Bardy | 2002/0095184 A1 | 7/2002 | Bardy et al. |
| 7,043,299 B2 | 5/2006 | Erlinger | 2002/0095188 A1 | 7/2002 | Mower |
| 7,050,851 B2 | 5/2006 | Plombon et al. | 2002/0103510 A1 | 8/2002 | Bardy et al. |
| 7,065,400 B2 | 6/2006 | Schechter | 2002/0107544 A1 | 8/2002 | Ostroff et al. |
| 7,065,407 B2 | 6/2006 | Bardy | 2002/0107545 A1 | 8/2002 | Rissmann et al. |
| 7,065,410 B2 | 6/2006 | Bardy et al. | 2002/0107546 A1 | 8/2002 | Ostroff et al. |
| 7,069,080 B2 | 6/2006 | Bardy | 2002/0107547 A1 | 8/2002 | Erlinger et al. |
| 7,076,296 B2 | 7/2006 | Rissmann et al. | 2002/0107548 A1 | 8/2002 | Bardy et al. |
| 7,079,988 B2 | 7/2006 | Albera | 2002/0107549 A1 | 8/2002 | Bardy et al. |
| 7,085,599 B2 | 8/2006 | Kim et al. | 2002/0107559 A1 | 8/2002 | Sanders et al. |
| 7,090,682 B2 | 8/2006 | Sanders et al. | 2002/0120299 A1 | 8/2002 | Ostroff et al. |
| 7,092,754 B2 | 8/2006 | Bardy et al. | 2002/0120311 A1 | 8/2002 | Lindh et al. |
| 7,096,064 B2 | 8/2006 | Deno et al. | 2002/0123769 A1 | 9/2002 | Panken et al. |
| 6,084,253 A1 | 9/2006 | Johnson et al. | 2002/0136328 A1 | 9/2002 | Shimizu |
| 7,103,404 B2 | 9/2006 | Stadler et al. | 2002/0138111 A1 | 9/2002 | Greenhut et al. |
| 7,107,093 B2 | 9/2006 | Burnes | 2002/0143263 A1 | 10/2002 | Shusterman |
| 7,110,817 B2 | 9/2006 | Yu et al. | 2002/0143264 A1 | 10/2002 | Ding et al. |
| 7,113,823 B2 | 9/2006 | Yonce et al. | 2002/0151808 A1 | 10/2002 | Schwartzman et al. |
| 7,117,036 B2 | 10/2006 | Florio | 2002/0183798 A1 | 12/2002 | Vonk |
| 7,120,495 B2 | 10/2006 | Bardy et al. | 2003/0004546 A1 | 1/2003 | Casey |
| 7,123,960 B2 | 10/2006 | Ding | 2003/0004552 A1 | 1/2003 | Plombon et al. |
| 7,127,290 B2 | 10/2006 | Girouard | 2003/0023175 A1 | 1/2003 | Arzbaecher et al. |
| 7,129,935 B2 | 10/2006 | Mackey | 2003/0036778 A1 | 2/2003 | Ostroff et al. |
| 7,139,610 B2 | 11/2006 | Ferek-Patric | 2003/0045904 A1 | 3/2003 | Bardy et al. |
| 7,144,586 B2 | 12/2006 | Levy et al. | 2003/0050671 A1 | 3/2003 | Bradley |
| 7,146,206 B2 | 12/2006 | Glass et al. | 2003/0069609 A1 | 4/2003 | Thompson |

| | | | |
|---|---|---|---|
| 2003/0083587 A1 | 5/2003 | Ferek-Petric | |
| 2003/0083710 A1 | 5/2003 | Ternes et al. | |
| 2003/0083711 A1 | 5/2003 | Yonce et al. | |
| 2003/0088278 A1 | 5/2003 | Bardy et al. | |
| 2003/0088279 A1 | 5/2003 | Rissmann et al. | |
| 2003/0088280 A1 | 5/2003 | Ostroff | |
| 2003/0088281 A1 | 5/2003 | Ostroff et al. | |
| 2003/0088282 A1 | 5/2003 | Ostroff | |
| 2003/0088283 A1 | 5/2003 | Ostroff | |
| 2003/0088286 A1 | 5/2003 | Ostroff et al. | |
| 2003/0097153 A1 | 5/2003 | Bardy et al. | |
| 2003/0204146 A1 | 10/2003 | Carlson | |
| 2003/0212436 A1 | 11/2003 | Brown | |
| 2004/0049235 A1* | 3/2004 | Deno et al. | 607/9 |
| 2004/0064159 A1* | 4/2004 | Hoijer et al. | 607/9 |
| 2004/0111021 A1 | 6/2004 | Olson | |
| 2004/0127950 A1 | 7/2004 | Kim et al. | |
| 2004/0158293 A1 | 8/2004 | Yonce et al. | |
| 2004/0162495 A1 | 8/2004 | Quenet et al. | |
| 2004/0171959 A1 | 9/2004 | Staler et al. | |
| 2004/0172065 A1 | 9/2004 | Sih et al. | |
| 2004/0215240 A1 | 10/2004 | Lovett et al. | |
| 2004/0215277 A1 | 10/2004 | Oosterhaoff et al. | |
| 2004/0220635 A1 | 11/2004 | Burnes | |
| 2004/0230128 A1 | 11/2004 | Brockway et al. | |
| 2004/0239650 A1 | 12/2004 | Mackey | |
| 2004/0243012 A1 | 12/2004 | Ciaccio et al. | |
| 2004/0243014 A1 | 12/2004 | Lee et al. | |
| 2004/0260351 A1 | 12/2004 | Holmstrom et al. | |
| 2004/0260522 A1 | 12/2004 | Albera | |
| 2005/0004612 A1 | 1/2005 | Scholten et al. | |
| 2005/0010120 A1 | 1/2005 | Jung | |
| 2005/0038478 A1 | 2/2005 | Klepfer et al. | |
| 2005/0043895 A1 | 2/2005 | Schechter | |
| 2005/0065587 A1 | 3/2005 | Gruzwa | |
| 2005/0107839 A1 | 5/2005 | Sanders | |
| 2005/0131477 A1 | 6/2005 | Meyer et al. | |
| 2005/0131478 A1 | 6/2005 | Kim et al. | |
| 2005/0131480 A1 | 6/2005 | Kramer et al. | |
| 2005/0137485 A1 | 6/2005 | Cao | |
| 2005/0137630 A1* | 6/2005 | Ding et al. | 607/9 |
| 2005/0137632 A1 | 6/2005 | Ding et al. | |
| 2005/0149134 A1 | 7/2005 | McCabe et al. | |
| 2005/0197674 A1 | 9/2005 | McCabe et al. | |
| 2005/0288600 A1 | 12/2005 | Zhang et al. | |
| 2006/0047319 A1* | 3/2006 | Bruhns et al. | 607/9 |
| 2006/0069322 A1 | 3/2006 | Zhang et al. | |
| 2006/0074331 A1 | 4/2006 | Kim et al. | |
| 2006/0111747 A1 | 5/2006 | Cazares et al. | |
| 2006/0111751 A1 | 5/2006 | Cazares | |
| 2006/0116593 A1 | 6/2006 | Zhang et al. | |
| 2006/0129194 A1 | 6/2006 | Zhang | |
| 2006/0129196 A1 | 6/2006 | Dong et al. | |
| 2006/0247695 A1 | 11/2006 | Stalsberg et al. | |
| 2006/0253043 A1 | 11/2006 | Zhang et al. | |
| 2006/0253044 A1 | 11/2006 | Zhang et al. | |
| 2006/0253164 A1 | 11/2006 | Zhang et al. | |
| 2007/0049974 A1 | 3/2007 | Li et al. | |
| 2007/0142737 A1 | 6/2007 | Cazares et al. | |
| 2008/0004665 A1 | 1/2008 | McCabe et al. | |
| 2008/0009909 A1 | 1/2008 | Sathaye et al. | |
| 2008/0045851 A1 | 2/2008 | Cazares et al. | |
| 2009/0076557 A1 | 3/2009 | Zhang et al. | |
| 2009/0198301 A1 | 8/2009 | Zhang et al. | |
| 2009/0312813 A1 | 12/2009 | Cazares | |

FOREIGN PATENT DOCUMENTS

| | | |
|---|---|---|
| EP | 1038498 | 9/2000 |
| EP | 1291038 | 3/2003 |
| EP | 1350539 | 10/2003 |
| EP | 1629863 | 3/2006 |
| WO | 92/17240 | 10/1992 |
| WO | WO9217240 | 10/1992 |
| WO | 92/20402 | 11/1992 |
| WO | WO9220402 | 11/1992 |
| WO | WO0240097 | 5/2002 |
| WO | WO0247761 | 6/2002 |
| WO | WO02087696 | 11/2002 |
| WO | 03/003905 | 1/2003 |
| WO | WO03003905 | 1/2003 |
| WO | WO03028550 | 4/2003 |
| WO | WO2004026398 | 4/2004 |
| WO | WO2005058412 | 6/2005 |
| WO | WO2005089865 | 9/2005 |
| WO | WO2006065707 | 6/2006 |
| WO | WO 2008/005270 * | 1/2008 |
| WO | WO2008005270 | 1/2008 |

OTHER PUBLICATIONS

U.S. Appl. No. 11/278,286, filed Jun. 29, 2006, Sathaye et al.
U.S. Appl. No. 11/312,280, filed Dec. 20, 2005, Cazares et al.
U.S. Appl. No. 11/506,253, filed Aug. 18, 2006, Cazares et al.
Acar et al., "SVD-based on-line exercise ECG signal orthogonalization", IEEE Transactions on Biomedical Engineering, vol. 46, No. 3, Mar. 1999. Abstract only.
2002, Splett et al. "Determination of Pacing Capture in Implantable Defibrillators: Benefit of Evoked Response Detection Using RC Coil to Can Vector," *PACE*, vol. 23, pp. 1645-1650. Abstract only.
Stirbis et al., *Optmizing the Shape of Implanted Artificial Pacemakers*, Kaunas Medical Institute. Translated from Meditsinskaya Tekhnika, No. 6, pp. 25-27 (1986). Abstract only.
2000, Splett et al. "Determination of Pacing Capture in Implantable Defibrillators: Benefit of Evoked Response Detection Using RV Coil to Can Vector," *PACE*, vol. 23, pp. 1645-1650.
U.S. Appl. No. 10/955,397, filed Sep. 30, 2004, Zhang et al.
U.S. Appl. No. 11/125,068, filed May 9, 2005, Zhang et al.
U.S. Appl. No. 11/478,286, filed Jun. 29, 2006, Sathaye et al.
A. Hyvärinen and E. Oja, *Independent Component Analysis: A Tutorial*, Helsinki Univ. of Technology, Apr. 1999.
Adel Belouchrani and Moeness G. Amin, *Blind Source Separation Based on Time-Frequency Signal Representations*, IEEE Transactions on Signal Processing, vol. 46, No. 11, pp. 2888-2897 (Nov. 1998).
Charles T. Leng et al., *Lead Configuration for Defibrillator Implantation in a Patient with Congenital Heart Disease and a Mechanical Prosthetic Tricuspid Valve*, PACE, vol. 24, No. 8, pp. 1291-1292 (Aug. 2001).
J.J. Rieta, et al., *Atrial Activity Extraction Based on Blind Source Separation as an Alternative to QRST Cancellation for Atrial Fibrillation Analysis*, Computers in Cardiology, vol. 27, pp. 69-72 (2000).
John C. Schuder et al., *Experimental Ventricular Defibrillation with an Automatic and Completely Implanted System*, Trans. Am. Soc. Artif. Int. Organs, vol. 16, pp. 207-212 (1970).
John C. Schuder et al., *Transthoracic Ventricular Defibrillation in the Dog with Truncated and Untruncated Exponential Stimuli*, IEEE Trans. on Bio-Medical Engin., vol. BME-18, No. 6, pp. 410-415 (Nov. 1971).
John C. Schuder et al., *Ventricular Defibrillation in the Dog Using Implanted and Partially Implanted Electrode Systems*, Am. J. of Cardiology, vol. 33, pp. 243-247 (Feb. 1974).
Karel Smits & Marek Malik, *Defibrillation Threshold (DFT) Model of a Fully Subcutaneous ICD System*, Europace Supplements, vol. 2, Jun. 2001 at col. 778, p. B83.
Krahn, A.D. et al. Recurrent syncope. Experience with an implantable loop record. Cardiol. Clin., vol. 15(2), May 1997, pp. 316-326.
Park & Pollock, *Use of an Implantable Cardioverter Defibrillator in an Eight-Month-Old Infant with Ventricular Fibrillation Arising from a Myocardial Fibroma*, PACE, vol. 22, No. 1, pp. 138-139 (Jan. 1999).
Philippe Gallois, et al., *Multi-Channel Analysis of the EEG Signals and Statistic Particularities for Epileptic Seizure Forecast*, Second Joint EMBS/BMES Conference, pp. 208-215 (Oct. 23-26, 2002).
Pierre Comon, *Independent component analysis, A new concept?*, Signal Processing, vol. 36, No. 3, pp. 287-314, (Apr. 1994).
Rainer Gradaus M.D. et al., *Nonthoracotomy Implantable Cardioverter Defibrillator Placement in Children: Use of a Subcutaneous Array Leads and Abdominally Placed Implantable Cardioverter Defibrillators in Children*, J. of Cardiovascular Electrophysiology, vol. 12, No. 3, pp. 356-360 (Mar. 2001).
Renee Hartz et al., *New Approach to Defibrillator Insertion*, J. Thoracic Cardiovascular Surgery, vol. 97, pp. 920-922 (1989).

Stirbis et al., *Optimization of the Shape of Implantable Electrocardiostimulators*. Kaunas Medical Institute. Translated from Meditsinskaya Tekhnika, No. 6, pp. 25-27 (1986).
Theofilos M. Kolettis, MD, PhD at al., *Submammary Implantation of a Cardioverter-Defibrillator with a Nonthoracotomy Lead System*, Am. Heart J., vol. 126, pp. 1222-1223 (Nov. 1993).
Vicente Zarzoso and Asoke K. Nandi, *Blind Separation of Independent Sources for Virtually Any Source Probability Density Function*, IEEE Transactions on Signal Processing, vol. 47, No. 9, pp. 2419-2432 (Sep. 1999).
Vicente Zarzoso and Asoke K. Nandi, *Noninvasive Fetal Electrocardiogram Extraction: Blind Separation Versus Adaptive Noise Cancellation*, IEEE Transactions on Biomedical Engineering, vol. 48, No. 1, pp. 12-18 (Jan. 2001).
Schuder et al., "Transthoracic Ventricular Defibrillation in the Dog with Truncated and Untruncated Exponential Stimuli", IEEE Transitions on Bio-Medical Engineering, vol. BME-18, No. 6, pp. 410-415, Nov. 1971.
Smits et al., "Defibrillation Threshold (DFT) Model of a Fully Subcutaneous ICD System, Europace Supplements", vol. 2, at col. 778, p. B83, Jun. 2001.
Wilkoff BL, et al., *Preventing Shocks after ICD Implantation: Can a Strategy of Standardized ICD Programming Match Physician Tailored?* Late Breaking Trials, HRS (2005).
Cohen et al. Capture Management Efficacy in children and young adults with endocardial and unipolar epicardial systems. Europace, vol. 6, pp. 248-255 (2004).
Office Action from U.S. Appl. No. 11/478,428 dated Nov. 3, 2009, 12 pages.
Office Action from U.S. Appl. No. 10/734,599 dated Sep. 21, 2009, 7 pages.
Office Action from U.S. Appl. No. 11/643,220 dated Nov. 17, 2009, 7 pages.
Appeal Decision from U.S. Appl. No. 11/124,950 dated Nov. 12, 2009, 14 pages.
Aug. 31, 2007, Restriction from U.S. Appl. No. 10/876,008 dated Mar. 27, 2007, 9 pages.
Restriction Response submitted May 29, 2007 to restriction dated Mar. 27, 2007 from U.S. Appl, No. 10/876,008, 18 pages.
Restriction from U.S. Appl. No. 10/876,008 dated Aug. 31, 2007, 11 pages.
May 29, 2007, Restriction Response submitted Oct. 1, 2007 to restriction dated Aug. 31, 2007 from U.S. Appl. No. 10/876,008, 14 pages.
Office Action from U.S. Appl. No. 10/876,008 dated Oct. 25, 2007, 22 pages.
Office Action Response submitted Jan. 23, 2008 to office action dated Oct. 25, 2007 from U.S. Appl. No. 10/876,008, 19 pages.
Office Action from U.S. Appl. No. 10/876,008 dated May 27, 2008, 11 pages.
Office Action Response submitted Jul. 28, 2008 to office action dated May 27, 2008 from U.S. Appl. No. 10/876,008, 15 pages.
Office Action Response with RCE submitted Sep. 28, 2008 to office action dated May 27, 2008 from U.S. Appl. No. 10/876,008, 15 pages.
Office Action from U.S. Appl. No. 10/876,008 dated Dec. 2, 2008, 6 pages.
Office Action Response submitted Feb. 16, 2009 to office action dated Dec. 2, 2008 from Appl. No. 10/876,008, 8 pages.
Office Action from U.S. Appl. No. 10/876,008 dated May 22, 2009, 10 pages.
Office Action Response submitted Aug. 13, 2009 to office action dated May 22, 2009 from U.S. Appl. No. 10/876,008, 12 pages.
Office Action from U.S. Appl. No. 10/955,397 dated Dec. 19, 2006, 10 pages.
Office Action Response submitted Mar. 19, 2007 to office action dated Dec. 19, 2006 from U.S. Appl. No. 10/955,397, 13 pages.
Office Action from U.S. Appl. No. 10/955,397 dated Jun. 7, 2007, 12 pages.
Appeal Brief submitted Oct. 25, 2007 from U.S. Appl. No. 10/955,397, 28 pages.
Examiner's Answer for U.S. Appl. No. 10/955,397, dated Jun. 11, 2008, 24 pages.
Appeal Decision from U.S. Appl. No. 10/955,397 dated Nov. 3, 2009, 13 pages.
Office Action from U.S. Appl. No. 10/955,397 dated Jan. 27, 2010, 12 pages.
Office Action from U.S. Appl. No. 11/079,744 dated Aug. 24, 2007, 13 pages.
Office Action Response submitted Nov. 20, 2007 to office action dated Aug. 24, 2007 from U.S. Appl. No. 11/079,744, 11 pages.
Office Action from patent application No. 11/079,744 dated Feb. 21, 2008, 8 pages.
Office Action Response submitted Apr. 17, 2008 to office action dated Feb. 21, 2008 from U.S. Appl. No. 11/079,744, 12 pages.
Office Action from U.S. Appl. No. 11/079,744 dated Jul. 3, 2008, 10 pages.
Office Action Response submitted Dec. 2, 2008 to office action dated Jul. 3, 2008 from U.S. Appl. No. 11/079,744, 13 pages.
Office Action from U.S. Appl. No. 11/079,744 dated Feb. 11, 2009, 11 pages.
Office Action Response submitted Apr. 9, 2009 to office action dated Feb. 11, 2009 from U.S. Appl. No. 11/079,744, 12 pages.
Office Action from U.S. Appl. No. 11/124,950 dated Dec. 19, 2006, 16 pages.
Office Action Response submitted Mar. 19, 2007 to office action dated Dec. 19, 2006 from U.S. Appl. No. 11/124,950, 9 pages.
Office Action from U.S. Appl. No. 11/124,950 dated Jun. 7, 2007, 8 pages.
Office Action Response submitted Aug. 7, 2007 to office action dated Jun. 7, 2007 from U.S. Appl. No. 11/124,950, 10 pages.
Examiner's Answer from U.S. Appl. No. 11/124,950 dated Jul. 10, 2008, 12 pages.
Notice of Allowance dated Feb. 26, 2010 from U.S. Appl. No. 11/124,950, 17 pages.
Office Action from U.S. Appl. No. 11/124,972 dated Sep. 13, 2007, 16 pages.
Office Action Response submitted Dec. 13, 2007 to office action dated Sep. 13, 2007 from U.S. Appl. No. 11/124,972, 13 pages.
Office Action from U.S. Appl. No. 11/124,972 dated Mar. 26, 2008, 11 pages.
Office Action Response submitted Jul. 28, 2008 to office action dated Mar. 26, 2008 from U.S. Appl. No. 11/124,972, 10 pages.
Office Action from U.S. Appl. No. 11/125,020 dated Dec. 19, 2006, 16 pages.
Office Action Response submitted Mar. 19, 2007 to office action dated Dec. 19, 2006 from U.S. Appl. No. 11/125,020, 9 pages.
Office Action from U.S. Appl. No. 11/125,020 dated Jun. 7, 2007, 10 pages.
Appeal Brief submitted Oct. 25, 2007 from U.S. Appl. No. 11/125,020, 23 pages.
Examiner's Answer for U.S. Appl. No. 11/125,020, dated May 5, 2008, 19 pages.
Appeal Decision from U.S. Appl. No. 11/125,020 dated Nov. 3, 2009, 13 pages.
Office Action from U.S. Appl. No. 11/125,068 dated Aug. 14, 2007, 18 pages.
Office Action Response submitted Jan. 14, 2008 to office action dated Aug. 14, 2007 from U.S. Appl. No. 11/125,068, 9 pages.
Office Action from U.S. Appl. No. 11/125,068 dated Apr. 21, 2008, 13 pages.
Office Action Response submitted Jun. 19, 2008 to office action dated Apr. 21, 2008 from U.S. Appl. No. 11/125,068, 12 pages.
Office Action from U.S. Appl. No. 11/478,428 dated Nov. 12, 2008, 21 pages.
Office Action Response submitted Mar. 5, 2009 to office action dated Nov. 12, 2008 from U.S. Appl. No. 11/478,428, 11 pages.
Office Action from U.S. Appl. No. 11/478,428 dated Jun. 1, 2009, 12 pages.
Office Action Response submitted Aug. 20, 2009 to office action dated Jun. 1, 2009 from U.S. Appl. No. 11/478,428, 11 pages.
Office Action Response submitted Mar. 3, 2010 to office action dated Nov. 3, 2009 from U.S. Appl. No. 11/478,428, 13 pages.
Examination Report for European patent application No. 04781543.6, dated Jul. 14, 2006, 3 pages.

Examination Report for European patent application No. 04781543.6, dated Feb. 8, 2007, 3 pages.
International Search Report and Written Opinion for International application No. PCT/US2005/022575 dated Nov. 2, 2005, 12 pages.
International Search Report and Written Opinion for International application No. PCT/US2005/035638, dated Feb. 27, 2006, 10 pages.
International Preliminary Report on Patentability from International application No. PCT/US2005/022575 dated Jan. 11, 2007, 7 pages.
International Search Report and Written Opinion for International application No. PCT/US2007/014968, dated Jun. 26, 2007, 15 pages.
Office Action Response dated Oct. 2, 2012 from U.S. Appl. No. 11/643,220, 12 pages.
Office Action dated May 15, 2012 for Japanese Application No. 2009-518259, 2 pages.
File History for U.S. Appl. No. 12/409,348.
File History for U.S. Appl. No. 11/643,220.
File History for U.S. Appl. No. 12/570,167.
International Search Report and Written Opinion dated May 4, 2011 from PCT Application No. PCT/US2009/059005, 14 pages.
Invitation to Pay Additional Fees dated Feb. 10, 2010 from PCT Application No. PCT/US2009/059005, 5 pages.
International Preliminary Report on Patentability dated May 19, 201 from PCT Application No. PCT/US2009/059005.
File History for U.S. Appl. No. 12/570,16.
Notice of Allowance dated Jul. 31, 2012 for U.S. Appl. No. 12/570,167, 6 pages.
Stirbis et al., Optimizing the Shape of Implanted Artificial Pacemakers, Kaunas Medical Institute. Translated from Meditsinskaya Tekhnika, No. 6, pp. 25-27, 1986.
Office Action dated Apr. 30, 2010 from U.S. Appl. No. 11/478,428, 14 pages.
Office Action Response dated Jun. 29, 2010 from U.S. Appl. No. 11/478,428, 13 pages.
Office Action dated Jul. 26, 2010 from U.S. Appl. No. 11/478,428, 3 pages.
Office Action Response dated Aug. 20, 2010 from U.S. Appl. No. 11/478,428, 11 pages.
Pre-Appeal Brief Statement dated Aug. 6, 2007 from U.S. Appl. No. 11/125,020, 6 pages.
Appeal Brief dated Feb. 11, 2008 from U.S. Appl. No. 11/125,020, 25 pages.
Reply Brief dated Jul. 7, 2008 from U.S. Appl. No. 11/125,020, 22 pages.
Office Action dated Mar. 23, 2010 from U.S. Appl. No. 11/125,020, 10 pages.
Office Action Response dated Jul. 20, 2010 from U.S. Appl. No. 11/125,020, 9 pages.
Office Action dated Sep. 29, 2010 from U.S. Appl. No. 11/125,020, 10 pages.
Pre-App Brief dated Aug. 6, 2007 from U.S. Appl. No. 10/955,397, 6 pages.
Appeal Brief dated Apr. 25, 2008 from U.S. Appl. No. 10/955,397, 24 pages.
Reply Brief dated Aug. 11, 2008 from U.S. Appl. No. 10/955,397, 28 pages.
Office Action dated Mar. 23, 2010 from U.S. Appl. No. 10/955,397, 11 pages.
Office Action Response dated Jul. 20, 2010 from U.S. Appl. No. 10/955,397, 13 pages.
Office Action dated Aug. 24, 2007 from U.S. Appl. No. 11/124,950, 3 pages.
Pre-Appeal Brief dated Oct. 11, 2007 from U.S. Appl. No. 11/124,950, 6 pages.
Appeal Brief dated Apr. 25, 2008 from U.S. Appl. No. 11/124,950, 24 pages.
Reply Brief dated Sep. 4, 2008 from U.S. Appl. No. 11/124,950, 11 pages.
Appeal Decision dated Nov. 12, 2009 from U.S. Appl. No. 11/124,950, 15 pages.
Notice of Allowance dated May 17, 2010 from U.S. Appl. No. 11/124,950, 7 pages.
Office Action dated Sep. 12, 2008 from U.S. Appl. No. 10/876,008, 3 pages.
Office Action Response dated Sep. 29, 2008 from U.S. Appl. No. 10/876,008, 15 pages.
Notice of Allowance dated Nov. 27, 2009 from U.S. Appl. No. 10/876,008, 7 pages.
Office Action dated Mar. 31, 2009 from U.S. Appl. No. 11/643,220, 7 pages.
Office Action Response dated Jul. 20, 2009 from U.S. Appl. No. 11/643,220, 13 pages.
Office Action Response dated Feb. 17, 2010 from U.S. Appl. No. 11/643,220, 10 pages.
Office Action dated Mar. 4, 2010 from U.S. Appl. No. 11/643,220, 3 pages.
Office Action Response dated Apr. 19, 2010 from U.S. Appl. No. 11/643,220, 11 pages.
Office Action dated Jun. 9, 2010 from U.S. Appl. No. 11/643,220, 10 pages.
Notice of Allowance dated Jul. 21, 2008 from U.S. Appl. No. 11/125,068, 4 pages.
Notice of Allowance dated Nov. 14, 2008 from U.S. Appl. No. 11/124,972, 4 pages.
International Preliminary Report on Patentability dated Jan. 6, 2009 from PCT Application No. PCT/US2007/014968, 8 pages.
International Preliminary Report on Patentability dated Apr. 3, 2007 from PCT Application No. PCT/US2005/035638, 5 pages.
Office Action Response dated Nov. 23, 2007 from U.S. Appl. No. 11/079,744, 11 pages.
Office Action dated May 18, 2009 from U.S. Appl. No. 11/079,744, 3 pages.

* cited by examiner

LOCAL AND NON-LOCAL SENSING FOR CARDIAC PACING

FIELD OF THE INVENTION

The present invention relates generally to cardiac pacing therapy, and more specifically, to methods and systems for timing the delivery of pacing pulses based on local and non-local sensing of cardiac signals.

BACKGROUND OF THE INVENTION

The healthy heart produces regular, synchronized contractions. Rhythmic contractions of the heart are normally initiated by the sinoatrial (SA) node, which is a group of specialized cells located in the upper right atrium. The SA node is the normal pacemaker of the heart, typically initiating 60-100 heartbeats per minute. When the SA node is pacing the heart normally, the heart is said to be in normal sinus rhythm.

Cardiac arrhythmia occurs when the heart rhythm is irregular or if the heart rate is too slow or too fast. During an arrhythmic episode, the heart's pumping action may become impaired and blood flow to peripheral tissues may be inadequate. Cardiac arrhythmias have a number of etiological sources, including tissue damage due to myocardial infarction, infection, or degradation of the heart's ability to generate or synchronize the electrical impulses that coordinate contractions.

Bradycardia occurs when the heart rhythm is too slow. This condition may be caused, for example, by impaired function of the SA node, denoted sick sinus syndrome, or by delayed propagation or blockage of the electrical impulse between the atria and ventricles. Bradycardia produces a heart rate that is too slow to maintain adequate circulation.

When the heart rate is too rapid, the condition is denoted tachycardia. Tachycardia may have its origin in either the atria or the ventricles. Tachycardia occurring in the atria of the heart, for example, includes atrial fibrillation and atrial flutter. Both conditions are characterized by rapid contractions of the atria. Besides being hemodynamically inefficient, the rapid contractions of the atria may also adversely affect the ventricular rate.

Ventricular tachycardia occurs, for example, when electrical activity arises in the ventricular myocardium at a rate more rapid than the normal sinus rhythm. Ventricular tachycardia may quickly degenerate into ventricular fibrillation. Ventricular fibrillation is a condition denoted by extremely rapid, uncoordinated electrical activity within the ventricular tissue. The rapid and erratic excitation of the ventricular tissue prevents synchronized contractions and impairs the heart's ability to effectively pump blood to the body, which is a fatal condition unless the heart is returned to sinus rhythm within a few minutes.

Implantable cardiac rhythm management systems have been used as an effective treatment for patients with serious arrhythmias, as well as for patients with conditions such as congestive heart failure. These systems typically include one or more leads and circuitry to sense signals from one or more interior and/or exterior surfaces of the heart. Such systems also include circuitry for generating electrical pulses that are applied to cardiac tissue at one or more interior and/or exterior surfaces of the heart. For example, leads extending into the patient's heart are connected to electrodes that contact the myocardium for sensing the heart's electrical signals and for delivering pulses to the heart in accordance with various therapies for treating arrhythmias.

Some implantable cardiac rhythm management systems include one or more endocardial leads which may include electrodes for both pacing and defibrillation. Such implantable cardiac rhythm management (CRM) systems are capable of delivering low energy pacing pulses to the heart at intervals sufficient to support the body's hemodynamic requirements. The CRM system may also deliver high-energy defibrillation shocks to the heart.

Cardiac pacing therapy involves the use of pacing timing intervals between pacing pulses delivered to various heart chambers. Appropriate specification of these and other timing intervals is desired to achieve optimal improvement of cardiac function. For the reasons stated above, and for other reasons stated below which will become apparent to those skilled in the art upon reading the present specification, there is a need in the art for methods and systems that provide for determination of timing intervals for cardiac pacing therapy. The present invention fulfills these and other needs.

SUMMARY OF THE INVENTION

The present invention is directed to systems and methods for determining pacing timing intervals based on the temporal relationship between the timing of local and non-local cardiac signal features. One embodiment is directed to a method for delivery of pacing therapy. At least one local cardiac electrical signal and at least one non-local cardiac electrical signal are sensed using body-implantable electrodes. The method involves sensing for a feature of the local signal corresponding to activation of a heart chamber and sensing for a feature of the non-local signal corresponding to the activation of the heart chamber. Delivery of one or more pacing pulses is based on a temporal relationship between timing of the feature of the local signal and timing of the feature of the non-local signal.

Some implementations involve beat by beat determination of pacing timing intervals. In these implementations, sensing the local signal and sensing the non-local signal involves sensing these signals during a cardiac cycle. The delivery of pacing pulses for the cardiac cycle is based on a temporal relationship between the timing of features of the local signal and the non-local signal.

According to one aspect of the invention, timing the delivery of the pacing pulses involves determining an atrioventricular delay based on the temporal relationship between the local feature timing and the non-local feature timing. In one implementation, the local cardiac signal is sensed from a local atrial site. A local P-wave is detected from the local signal and a non-local P-wave is detected from the non-local signal. The delivery of the pacing pulses is timed based on the temporal relationship between the local P-wave and the non-local P-wave.

In another implementation, the local cardiac signal is sensed from a local atrial site. A local P-wave is detected from the local signal and a non-local P-wave is detected from the non-local signal. Timing delivery of the pacing pulses involves initiating the atrioventricular delay based on the detection of the local P-wave and ending the atrioventricular delay based on the detection of the non-local P-wave.

Various implementations of the invention involve delivery of trigger pacing. Pacing may be triggered to a single heart chamber or to contralateral heart chambers. For example, delivery of a pacing pulse may be triggered based on the timing of the non-local feature if the non-local feature is detected. If the non-local feature is not detected, the pacing pulse may be triggered based on the timing of the local feature. More specifically for atrial pacing, pacing may be triggered to one or more atria based on the timing of a non-local P-wave if the non-local P-wave is detected. If the non-local P-wave is not detected, pacing may be triggered based on the timing of a local P-wave. For ventricular pacing, pacing may be triggered to one or more ventricles based on the timing of a non-local QRS complex if the non-local QRS complex is detected. If the non-local QRS complex is not detected, pacing may be triggered based on the timing of a local QRS complex.

Another embodiment of the invention is directed to an implantable cardiac rhythm management device. The implantable device includes a plurality of implantable electrodes electrically coupled to the heart. At least a first pair of the plurality of electrodes is configured to sense a local cardiac signal. At least a second pair of the plurality of electrodes is configured to sense a non-local cardiac signal. Sense circuitry is coupled to the first and second electrode pairs and is configured to sense a local cardiac signal via the first electrode pair and a non-local cardiac signal via the second electrode pair. Detection circuitry is configured to detect a feature of the local signal associated with activation of a heart chamber and to detect a feature of the non-local signal associated with activation of the heart chamber. A control processor times delivery of one or more pacing pulses based on a temporal relationship between timing of the local signal feature and timing of the non-local signal feature.

For example at least one electrode of the second pair of electrodes may comprise a ring electrode, a defibrillation coil, or a subcutaneous, non-intrathoracic electrode.

According to one aspect of the invention, the local signal feature comprises a local P-wave and the non-local signal feature comprises a non-local P-wave. The control processor is configured determine an atrioventricular delay based on the temporal relationship between the timing of the local P-wave and the timing of the non-local P-wave. The atrioventricular delay is used to time delivery of the one or more pacing pulses. According to various aspects, the control processor may be configured to determine the atrioventricular delay based on the temporal relationship between a beginning, end, or peak timing of the local P-wave and a beginning, end, or peak timing of the non-local P-wave.

According to one aspect of the invention, the control processor is configured to trigger pacing based on the timing of the non-local signal feature if the non-local signal feature is detected and to trigger pacing based on the timing of the local signal feature if the non-local signal feature is not detected.

The pacing pulses may be delivered as part of a bradycardia pacing therapy, an atrioventricular pacing therapy and/or a resynchronization pacing therapy.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
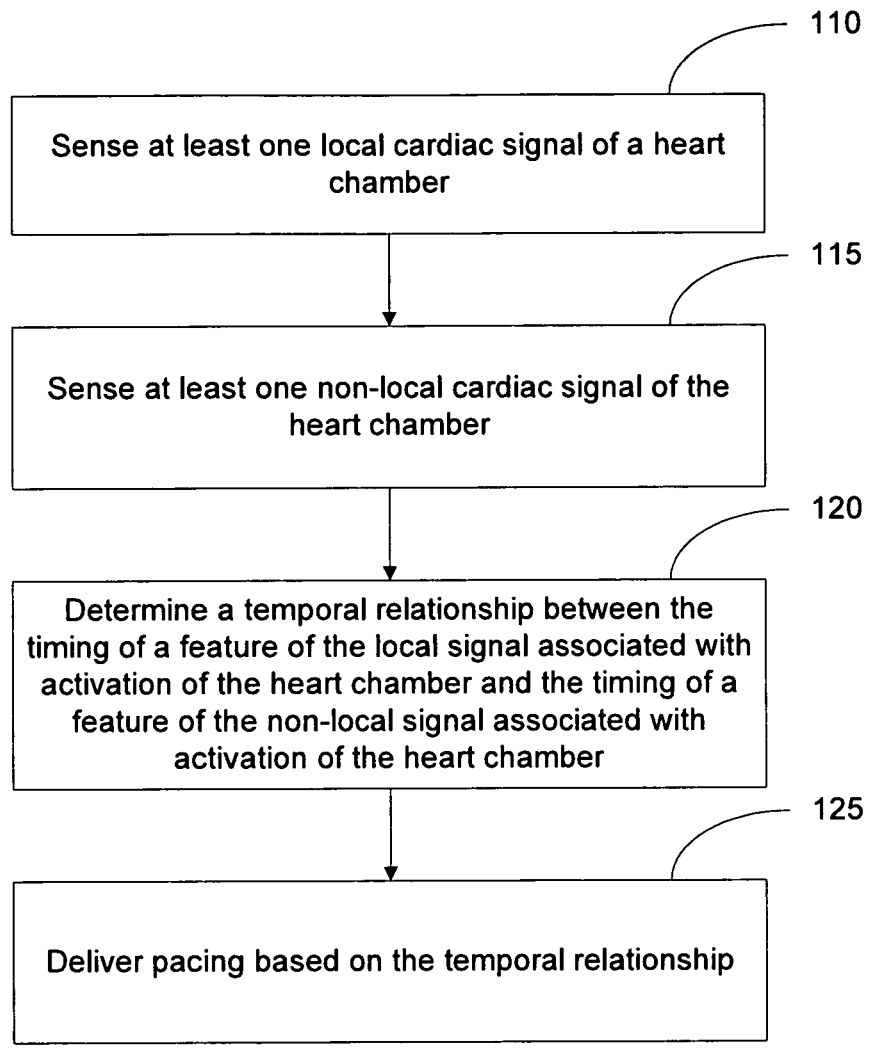
FIG. 1A is a flow diagram illustrating a method of determining pacing timing in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

Systems, devices or methods according to the present invention may include one or more of the features, structures, methods, or combinations thereof described hereinbelow. For example, a device or system may be implemented to include one or more of the advantageous features and/or processes described below. It is intended that such device or system need not include all of the features described herein, but may be implemented to include selected features that provide for useful structures and/or functionality. Such a device or system may be implemented to provide a variety of therapeutic or diagnostic functions.

Mechanical contractions in the heart are triggered by waves of electrical depolarization that travel through the cardiac tissue. In a healthy heart, a depolarization wave for each cardiac cycle is initiated at the sinoatrial node and travels through specialized fibers to the heart chambers to cause synchronized contractions of the heart chambers. Due to disease, damage from myocardial infarction, and/or other degradation, the pathways and/or tissues involved in conduction of the depolarization wavefront may become compromised.

Pacemakers deliver electrical pacing pulses to the heart to produce contractions of the heart chambers in synchrony and at a rate sufficient to meet metabolic demand. Pacing therapy involves the implementation of timing intervals between various events during a cardiac cycle. The timing intervals may be used to control the rate of heart chamber contractions and/or the synchrony between heart chamber contractions. For example, for patients whose intrinsic heart rate is too slow, pacing assists the heart in contracting at a rate that is sufficient to provide blood flow to meet the patient's metabolic requirements. For patients suffering from congestive heart failure (CHF), cardiac pacing may be used to ensure that the contractions of the heart chambers occur in a timed sequence that improves heart function.

Pacemakers typically include cardiac electrodes that are in electrical contact with the myocardium and sense local cardiac electrical signals. The electrodes are used to sense cardiac electrical signals, such as cardiac signals associated with intrinsic or evoked cardiac depolarization events. Pacemakers that stimulate the heart according to timing intervals based on sensed cardiac events are capable of producing cardiac cycles that more closely mimic the physiological operation of a normal heart.

A cardiac electrical signal provides information about the depolarization status of the heart. Local sensing of cardiac signals may be achieved via electrodes that make contact with the cardiac myocardium. Local sensing using an electrode in contact with the myocardial tissue yields signals that are most strongly representative of the activation signals that are present close to the site of the electrode. Non-local sensing of the cardiac signals may be achieved via electrodes that are electrically coupled to, but do not make directed contact with, the myocardium. A sensed non-local cardiac activation signal is effectively a superposition of a number of activation signals occurring within the heart that are associated with a cardiac contraction.

In implantable pacemakers, tip electrodes which are configured to make direct contact with the myocardium, have traditionally been used for local sensing. Non-local sensing may be accomplished via various electrode pairs of an implantable pacemaker or defibrillator, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). For example, electrode pairs suitable for non-local sensing include RV-ring to RV-coil, RV-ring to SVC-coil, RV-ring to RA-ring, or may include sensing between two can electrodes, between a can electrode and an indifferent electrode, or between a can or indifferent electrode and a ring or coil electrode. An electrode pair, as used herein, refers to at least two electrodes, wherein each electrode of the pair may comprise multiple electrodes and/or multiple electrode elements used for sensing.

In some situations, the particular placement of a ring, coil, or other electrode configured for non-local sensing may cause the electrode to make direct contact with the myocardium. In these situations, unintentional local sensing is apparent from the cardiac waveform morphology and use of the electrode in conjunction with pacing parameter determination via non-local sensing in accordance with embodiments of the present invention may be avoided.

Embodiments of the invention are directed to systems and methods for timing the delivery of one or more pacing pulses based on sensed signals from local and non-local cardiac sites. The flow diagram of FIG. 1A illustrates a method of determining pacing timing in accordance with embodiments of the invention. At least one local cardiac signal is sensed 110 from at least one local cardiac site. At least one non-local cardiac signal is sensed 115 from at least one non-local site. A temporal relationship is determined 120 between the timing of a feature of the local signal associated with activation of a heart chamber and the timing of a feature of the non-local signal associated with activation of the heart chamber. Pacing is delivered 125 based on the temporal relationship.

Figure 1B:
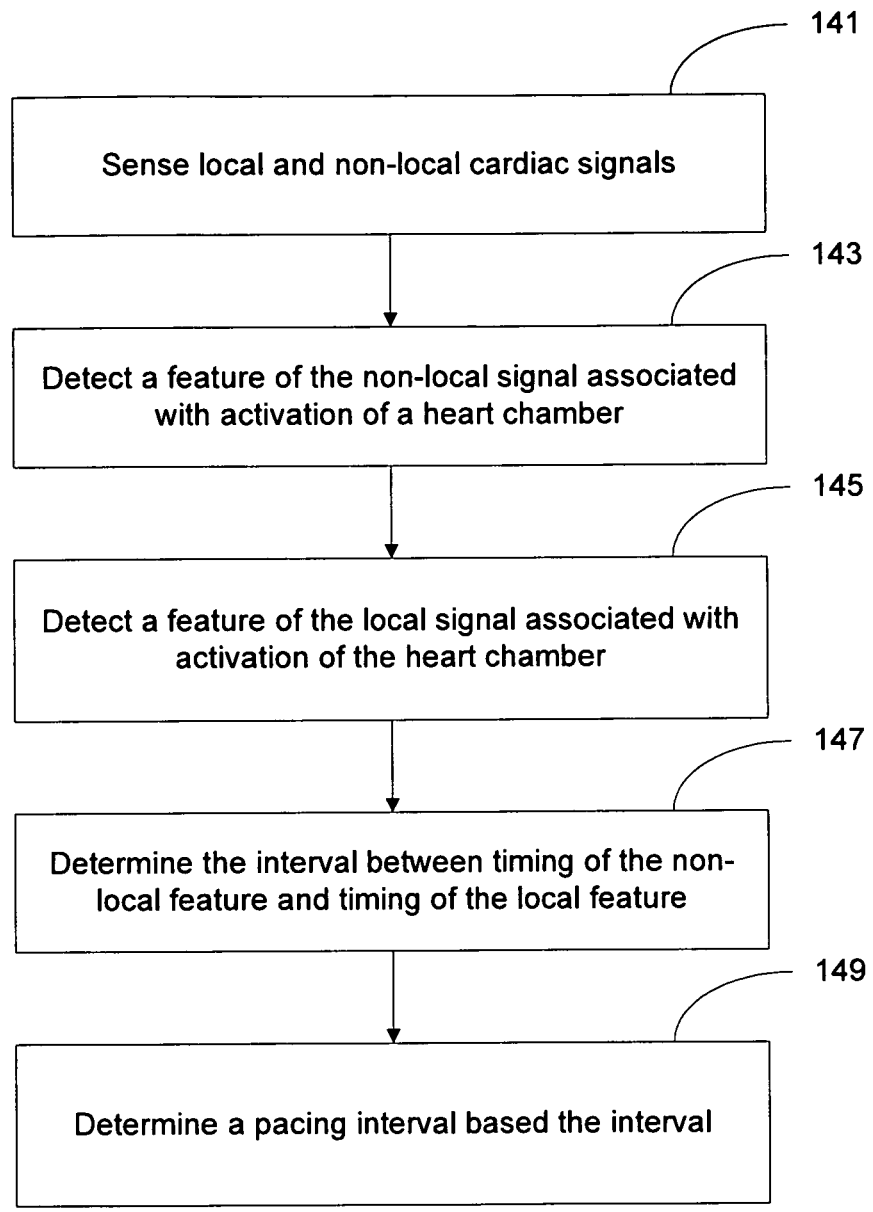
FIG. 1B is a flow diagram illustrating a method for determination of a pacing timing interval based on the interval between features of the local and non-local signals in accordance with embodiments of the invention.

According to some implementations, the local signal feature and the non-local signal feature are detected and the temporal relationship is determined as the interval of time between the local and non-local features. The flow diagram of FIG. 1B illustrates a method for determining a pacing interval, such as an atrioventricular delay, based on the time interval between features of the local and non-local signals in accordance with various embodiments. Local and non-local cardiac signals are sensed 141. A feature of the non-local signal associated with activation of a heart chamber is detected 143. A feature of the local signal associated with activation of the heart chamber is detected 145. The interval between the timing of the non-local signal feature and the timing of the detected local signal feature is determined 147. A pacing interval is determined 149 based on the interval between the non-local and local signal features.

In some implementations, both local and non-local signals are sensed and pacing is triggered based on detection of either a non-local signal feature or a local signal feature. For example, detection of a non-local feature may trigger pacing to one or more heart chambers. A feature of the local signal, which may be more reliably detected than the non-local feature, may be used to trigger pacing in the absence of detection of the non-local signal feature. In one example, sensing of both local and non-local signals is employed, but a feature of only one of the cardiac signals is detected and used to trigger the pacing.

Figure 1C:
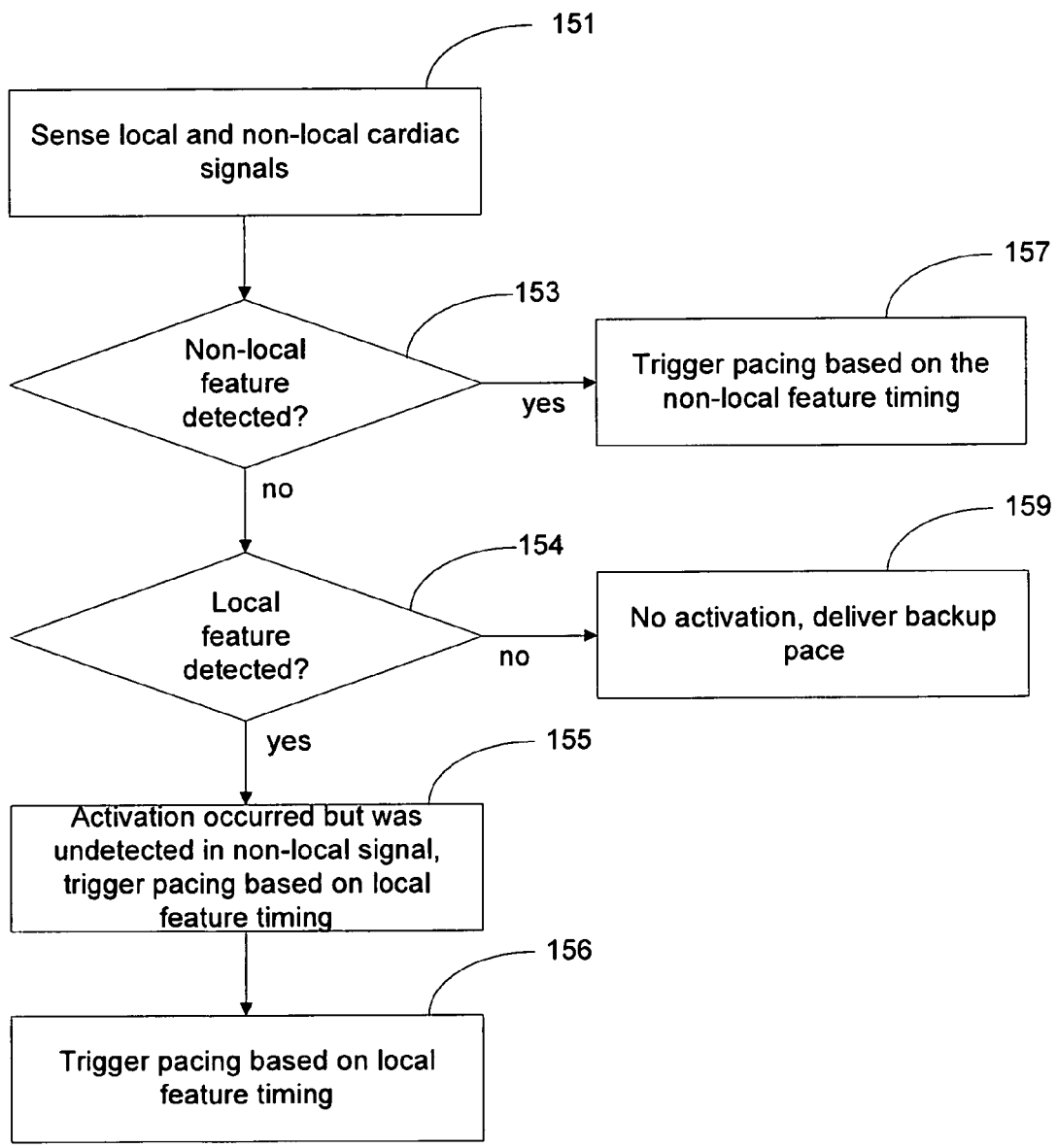
FIG. 1C is a flow diagram illustrating trigger pacing based on local and non-local signals in accordance with embodiments of the invention.

An embodiment directed to trigger pacing that relies on sensing both local and non-local signals is illustrated in the flow diagram of FIG. 1C. Both local and non-local signals are sensed 151. Detection 153 of a non-local signal feature associated with activation of a heart chamber triggers 157 delivery of a pacing pulse. In this embodiment, the non-local signal feature which is associated with activation of a heart chamber occurs prior to the local signal feature associated with activation of the heart chamber. If a non-local feature is not detected 153 and a local feature is detected 154, the system determines that activation has occurred, but the non-local feature was not detected 155. Pacing is triggered 156 based on the detected local signal feature. If no activation is detected from either the local or non-local signals, a backup pace may be delivered 159.

In various implementations, the delivery of one or more pacing pulses may be timed based on a pacing timing interval such as an atrioventricular timing interval, an interatrial timing interval and/or an interventricular timing interval. An atrioventricular pacing delay is a timing interval between an atrial sensed or paced event and delivery of a ventricular pace. The atrial event may be a right atrial event or a left atrial event and the ventricular pace may be a right ventricular pace or a left ventricular pace. An interatrial pacing delay is a timing interval between a sensed or paced event in one atrium and a pace delivered to the other atrium. An interventricular pacing delay is a timing interval between a sensed or paced event in one ventricle and a pace delivered to the other ventricle. Pacing pulses may be delivered to each of the electrodes in a timed sequence according to interchamber pacing delays that improve the contractile function. Timing the delivery of pacing pulses based on non-local sensing is particularly advantageous for cardiac resynchronization therapy because non-local sensing provides information about left chamber (e.g., left atrial) contractions without the need for local placement of left chamber sense electrodes.

Figure 2A:
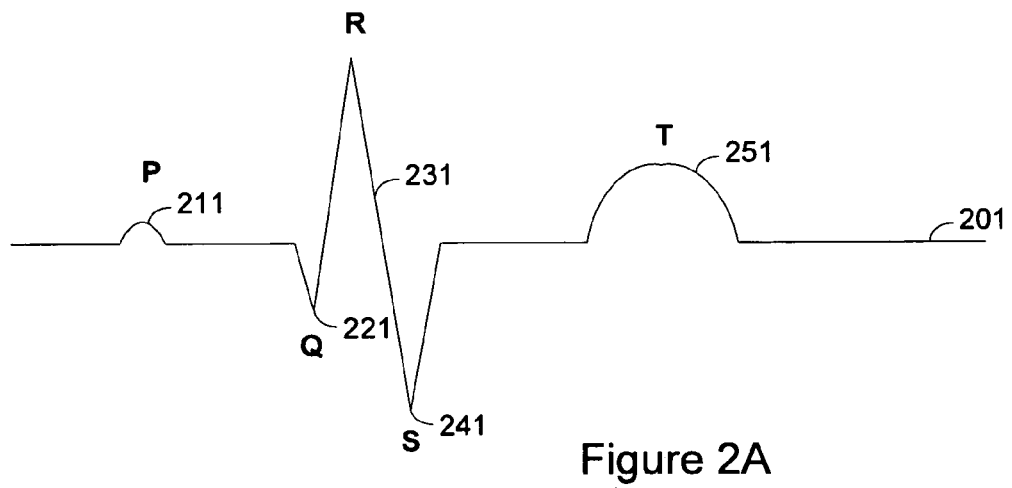
FIGS. 2A-2B illustrate local and non-local cardiac signals which may be used for timing the delivery of pacing pulses in accordance with embodiments of the invention.
Figure 2B:
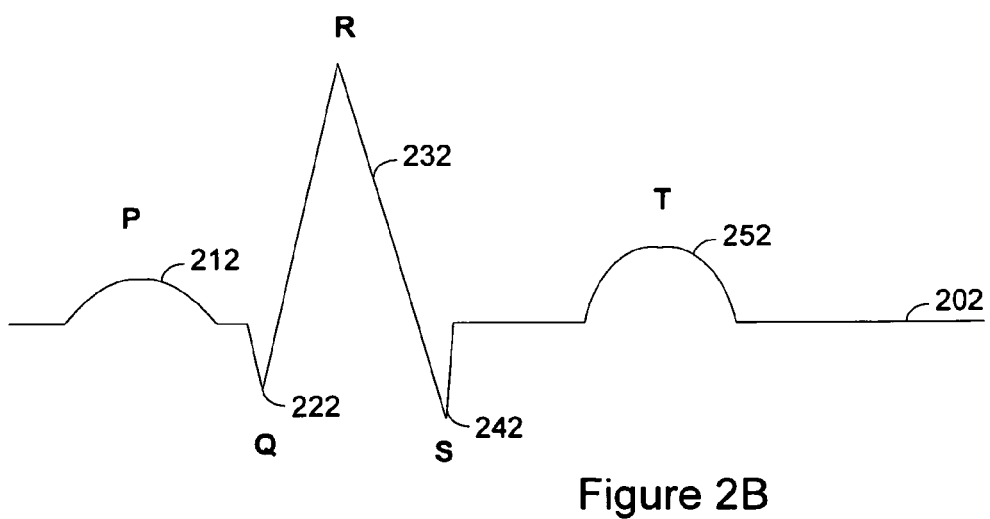

FIGS. 2A-2B illustrate local and non-local cardiac signals which may be used for timing the delivery of pacing pulses. FIGS. 2A and 2B illustrate cardiac signals 201, 202 sensed from a local site and a non-local site, respectively. In some implementations the local 201 and non-local 202 signals are sensed simultaneously. The portion of the cardiac signals 201, 202 representing activation of the atrial muscle fibers is referred to as a P-wave 211, 212. Activation of the ventricular muscle fibers is collectively represented by Q 221, 222, R 231, 232, and S 241, 242 waves of the cardiac signals 201, 202. The Q 221, 222, R 231, 232, and S 241, 242 waves are typically referred to collectively as the QRS complex, which is a well-known morphologic feature of electrocardiograms. Finally, the portion of the signal representing repolarization of the ventricular muscle fibers is known as a T wave 251, 252. Between contractions, the cardiac signal returns to an isopotential level during the T-wave 251, 252.

The cardiac signal 201 illustrated in FIG. 2A is typical of a local signal sensed using an electrode in contact with the myocardium. The cardiac signal 202 illustrated in FIG. 2B is typical of a non-local cardiac electrical signal, which is effectively a superposition of a number of activation signals. The cardiac signal 202 may be obtained via a non-local electrode pair electrically coupled to, but not in direct contact with, the myocardium.

Non-local sensing is particularly useful, for example, because it provides information about activation of the left atrium. Cardiac pacemakers providing resynchronization therapy typically include one or more electrodes in the right atrium for local sensing of right atrial activation signals. An atrioventricular delay (AVD) is initiated upon sensing an intrinsic depolarization of the right atrium or a right atrial pace. One or both ventricles are paced following the AVD. In some current devices, the conduction time delay resulting from paced or sensed atrial beats is accounted for by setting a fixed AVD based on population statistics and initiated by local right atrial sensing. A fixed AVD based on local right atrial sensing alone may not be appropriately timed to take into account a particular patient's interatrial conduction time. Further, if the atrium is paced, the atrial pacing results in a non-physiologic activation sequence that may further prolong activation of the atrium. If the fixed AVD is inappropriately programmed, the hemodynamic synchronization between atrial and ventricular contractions is sub-optimal.

The non-local signal provides information about left atrial activation timing and may be used in conjunction with the local signal to determine an AVD tailored to a particular patient and/or tailored to a particular type of pacing cycle. A pacing cycle in which one or both atria are paced may use an AVD having a different duration than a pacing cycle in which the atria are not paced. As described herein, local and non-local sensing may be used to provide a dynamically adjustable AVD. In some implementations, the duration of the AVD may be determined based at least in part on the timing of the end of the non-local P-wave. In some implementations, the AVD may be determined based on the temporal relationship between the timing of the end of the local P-wave and the timing of a feature of the non-local P-wave.

Embodiments of the present invention provide pacing timing optimization approaches that are patient specific and allow dynamic adjustment of interchamber pacing delays.

According to various embodiments, timing information associated with features of the local and non-local signals may be used to determine pacing timing delays. For example, timing intervals may be based on the relationship between feature points, such as the start, end, or peak value, of the local signal and feature points, such as the start, end, or peak value, of the non-local signal. The timing of the delivery of pacing pulses may be based on widths of various features. In one implementation, the length of the AVD, which determines the timing of the delivery of a ventricular pacing pulse, is related to the P-wave width of the non-local signal. The non-local P-wave width is representative of the conduction delay between the right and left atria. Generally, a relatively larger P-wave width indicates a longer conduction delay in the activation signals propagating between the atria. Using the non-local P-wave width in the determination of the AVD allows for synchronous atrioventricular pacing so that pacing pulses are delivered to one or both ventricles at an optimal time following the atrial contraction. Improved timing of ventricular pacing improves cardiac pumping action and increases output.

In some configurations, adjustment of the pacing timing intervals may be performed for each cardiac cycle on a beat by beat basis. In some configurations, one or more pacing timing intervals may be determined using data collected from local and non-local signals of previous cardiac cycles.

Figure 3:
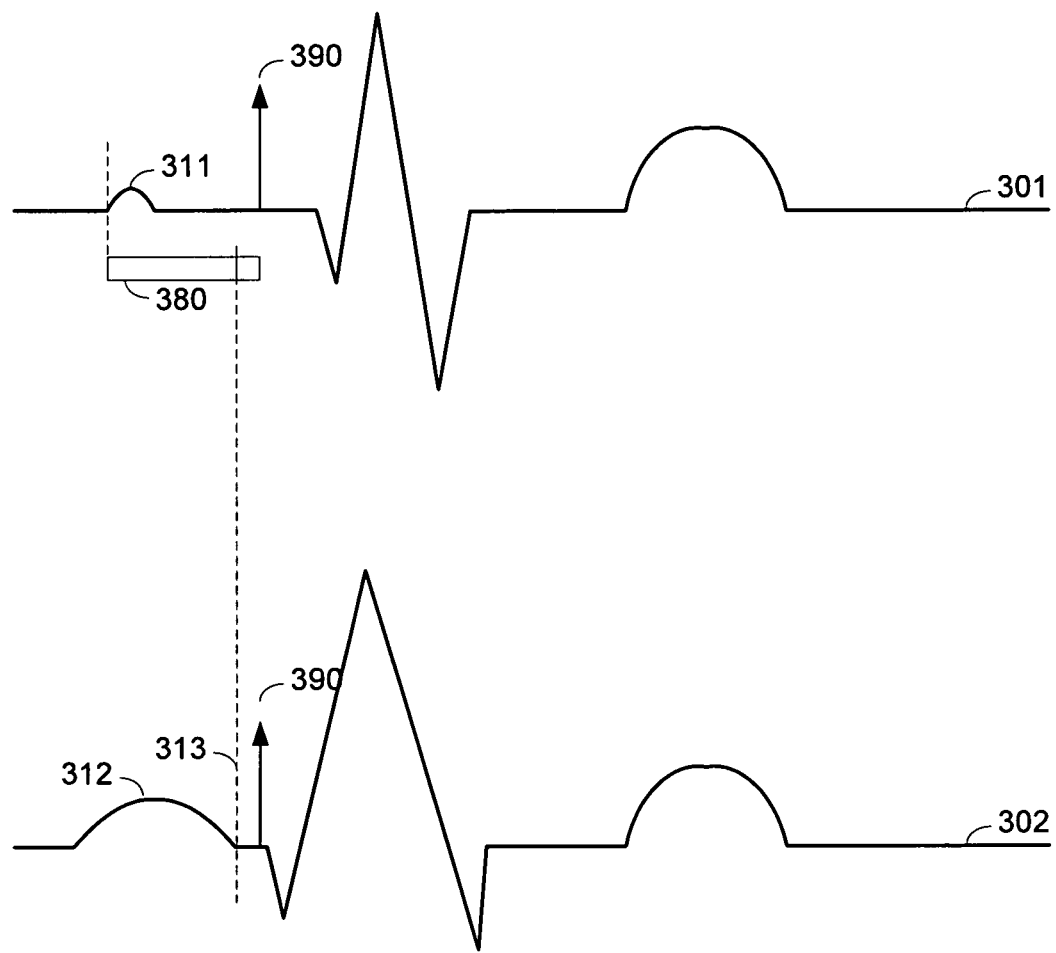
FIG. 3 shows graphs of local and non-local signals illustrating the determination of an atrioventricular delay (AVD) in accordance with embodiments of the invention.
Figure 4:
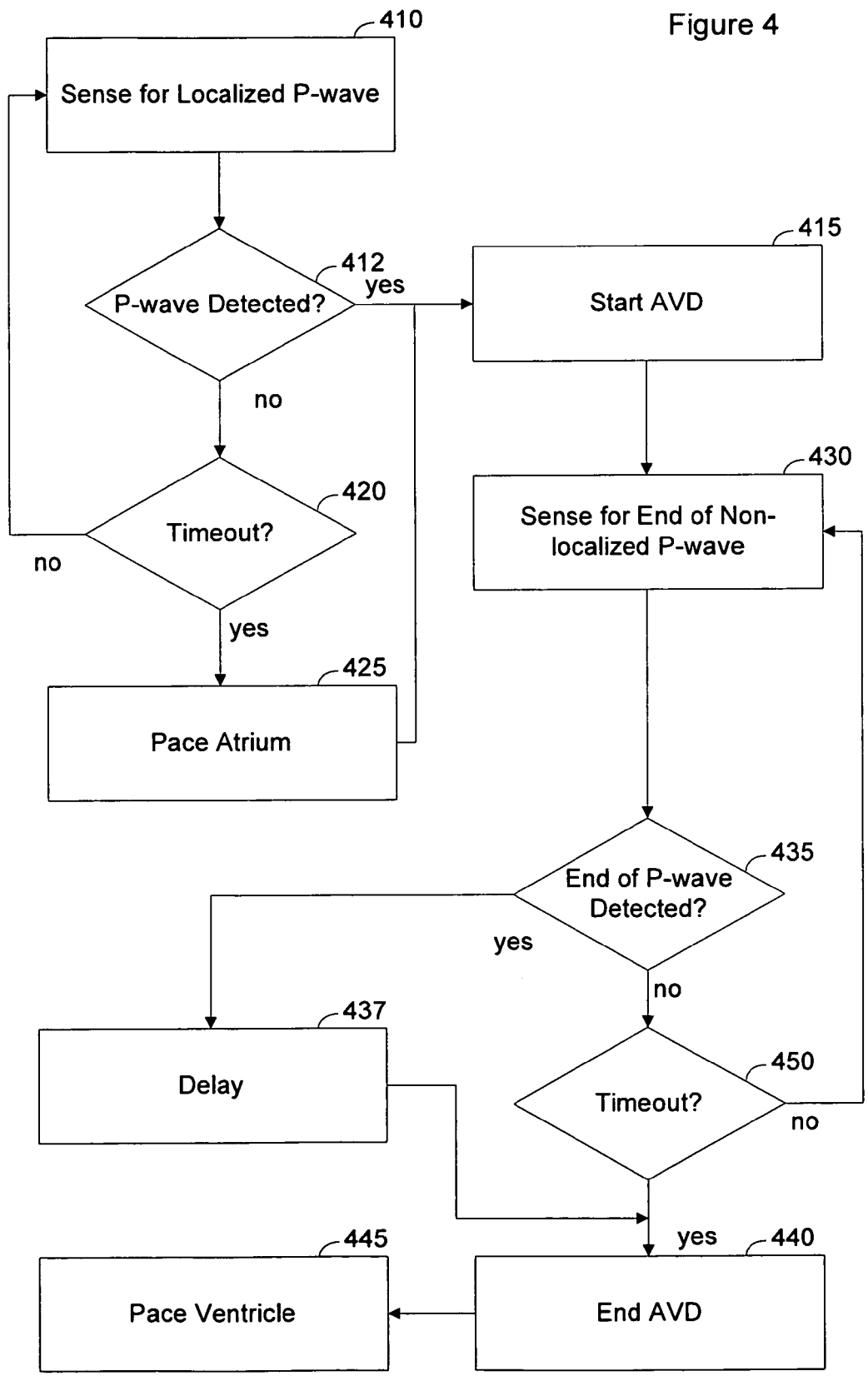
FIG. 4 is a flow diagram illustrating a method for beat by beat adjustment of AVD based on P-waves detected from local and non-local signals of each cardiac cycle in accordance with embodiments of the invention.

One example, illustrated by the graph of FIG. 3 and the flow diagram of FIG. 4, involves the beat by beat adjustment of AVD based on P-waves detected from both the local 301 and non-local 302 signals of each cardiac cycle. The device senses for a P-wave 311 on the local signal 301 and initiates an AVD 380 if the local P-wave 311 is detected. The device detects the end 313 of the non-local P-wave 312. Following a predetermined interval from the end 313 of the non-local P-wave 312, the AVD 380 ends and a pacing pulse 390 is delivered to a ventricle. In some embodiments, the AVD 380 is dynamically adjusted beat by beat using the process described above based on the detection of the local P-wave 311 and the timing of the end 313 of the non-local P-wave 312.

Beat by beat adjustment of the AVD based on local and non-local P-waves is further illustrated by the flowchart of FIG. 4A. The device senses for 410 a P-wave on the local signal. If the local P-wave is detected 412, then the AVD delay is started 415. If a timeout interval is exceeded 420 while sensing for the local P-wave, then the atrium is paced 425.

The device senses 430 for the end of a non-local P-wave. If the non-local P-wave is detected 435, then the AV delay ends 440 after a predetermined time delay 437 and a pacing pulse is delivered 445 to one or both ventricles. The predetermined time delay may be zero or may be greater than zero and less than about 300 msec, for example. Selection of the predetermined time delay may be based on clinical data or on individualized data from the patient, such as interchamber conduction data. Particularly for CHF patients, the predetermined time delay may be selected to produce optimal cardiac pumping function and/or reduce the symptoms of CHF. The predetermined time delay may be adjustable based on acute or chronic factors, such as the patient's metabolic demand or disease progression.

If, while waiting for the end of the non-local P-wave, a timeout interval is exceeded 450, then the AVD ends 440 and a pacing pulse is delivered 445 to one or both ventricles.

Figure 5:
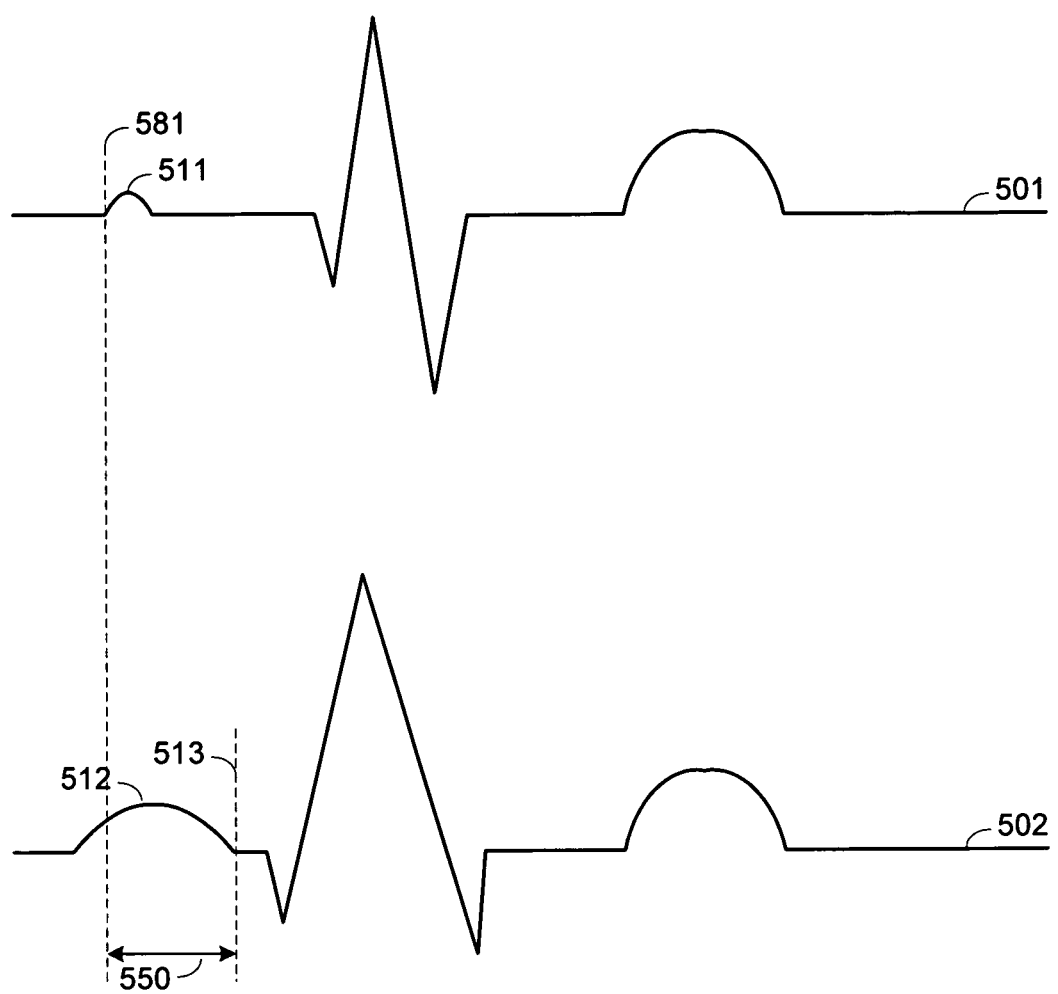
FIG. 5 is a graph illustrating determination of AVD for a cardiac cycle based on the local and non-local signal features of one or more previous cardiac cycles in accordance with embodiments of the invention.

The graph of FIG. 5 illustrates a method for determining the AVD according to another embodiment. In this embodiment, local 501 and non-local 502 signals are sensed for one or more cardiac cycles. The system searches for a feature point 581 of the local P-wave 511, such as the start, end, or peak of the local P-wave. In the example illustrated in FIG. 5, the system searches for the beginning 581 of the local P-wave. The system searches a feature point of the non-local P-wave 512, such as the end 513 of the non-local P-wave 512. The interval 550 between the beginning 581 of the local P-wave 511 and the end 513 of the non-local P-wave 512 is measured for one or multiple cardiac cycles. The AVD is determined based on the measured intervals 550. For example, the AVD may be determined based on a median, mean, or weighted average of the measured intervals. The device uses the AVD for subsequent cardiac cycles. Periodically, the AVD may be updated using the process described above.

In some embodiments, a number of AVDs may be determined as described in FIG. 5 for different heart rates. The AVDs may be indexed by rate and stored. If a particular heart rate is detected, an AVD corresponding to the particular rate may be selected for use. Different AVDs may be determined for intrinsic and paced beats. Use of both the local and non-local signals for determination of the AVD as described herein produces pacing that is consistent for intrinsic and paced beats. The determination of AVD based on non-local sensing provides the ability to react to cases in which the atrial lead position results in shorted paced P-waves, as has been shown in lower atrial septal pacing.

In some embodiments, timing the delivery of pacing pulses involves triggering pacing of a heart chamber or contralateral heart chambers based on one or more signal features. This implementation is particularly useful for triggered ventricular pacing in patients having prolonged interatrial conduction times and ventricular conduction abnormalities. In these patients, activation of the ventricles may precede sensed activation at the local ventricular sense electrode. As described more fully below, the non-local signal may be used to detect the first activation of the ventricles. Biventricular pacing may be triggered based on the first ventricular activation detected via the non-local signal. Biventricular trigger pacing as provided by this embodiment uses intrinsic conduction to activate the septum and promote fusion between intrinsically conducted activation and paced ventricular activity to achieve optimized cardiac performance for individual patients.

Figure 6:
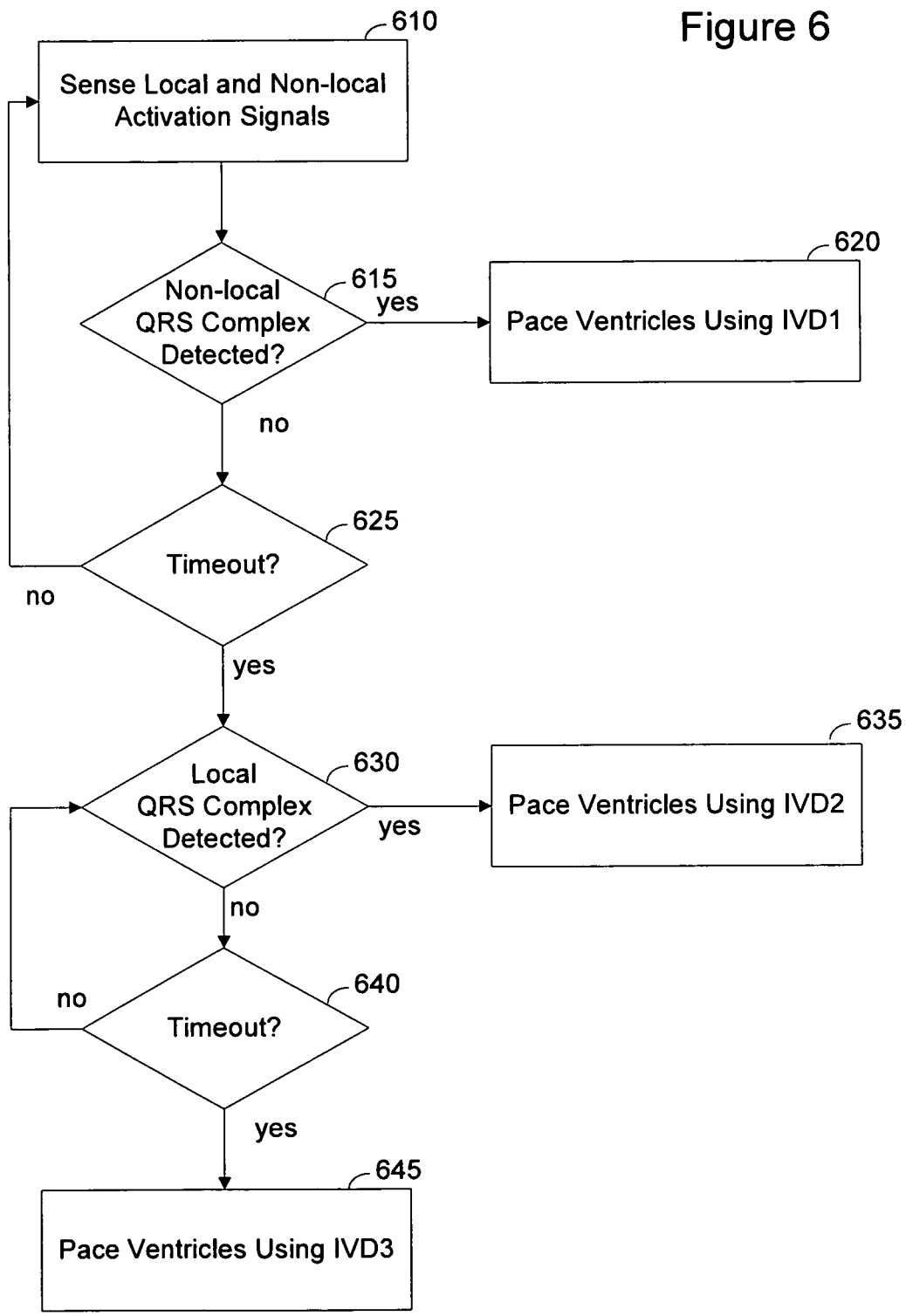
FIG. 6 is a flow diagram of a method for implementing triggered pacing with backup pacing in accordance with an embodiment of the invention.

The flowchart of FIG. 6 illustrates ventricular pacing triggered by a feature point of the non-local signal with backup pacing implemented using a pacing timing delay initiated by a local signal. Although the example of FIG. 6 is directed to triggered ventricular pacing, a similar process may be implemented for triggered atrial pacing. The device senses 610 signals from a local ventricular site and a non-local site. If the initiation of a QRS complex is detected 615 on the non-local signal, pacing is triggered 620 to one or both ventricles. The ventricles are paced using a first interventricular delay IVD1. If the initiation of the QRS complex is not detected 615, and a timeout has occurred 625, then an alternate process for timing ventricular pacing is used. If the QRS complex has been detected 630 on the local right ventricular signal, then the left ventricle is paced 635 using IVD2. If the right ventricular QRS complex is not detected 640 following a timeout period, then the right and left ventricles are paced 645 using IVD3.

In some embodiments, IVD1, IVD2, and IVD3 may have the same duration. In other embodiments, one or more of the IVDs used in the above example may be selected to achieve optimal cardiac output for the particular pacing timing situation. The IVDs may be determined, for example, from previously detected local and/or non-local signals. The IVDs may be determined based on the QRS complex width of the non-local signal, or the interval between a local signal feature point and a non-local signal feature point, or by other methods.

A wide variety of implantable cardiac stimulation devices may be configured to sense local and non-local signals and time the delivery of pacing pulses in accordance with the present invention. A non-limiting, representative list of such devices includes pacemakers, cardiovertors, defibrillators, resynchronizers, and other cardiac therapy delivery devices. These devices may be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). A cardiac therapy device implemented in accordance with the present invention may incorporate one or more of the electrode types identified above and/or combinations thereof to sense local and non-local signals.

Figure 7:
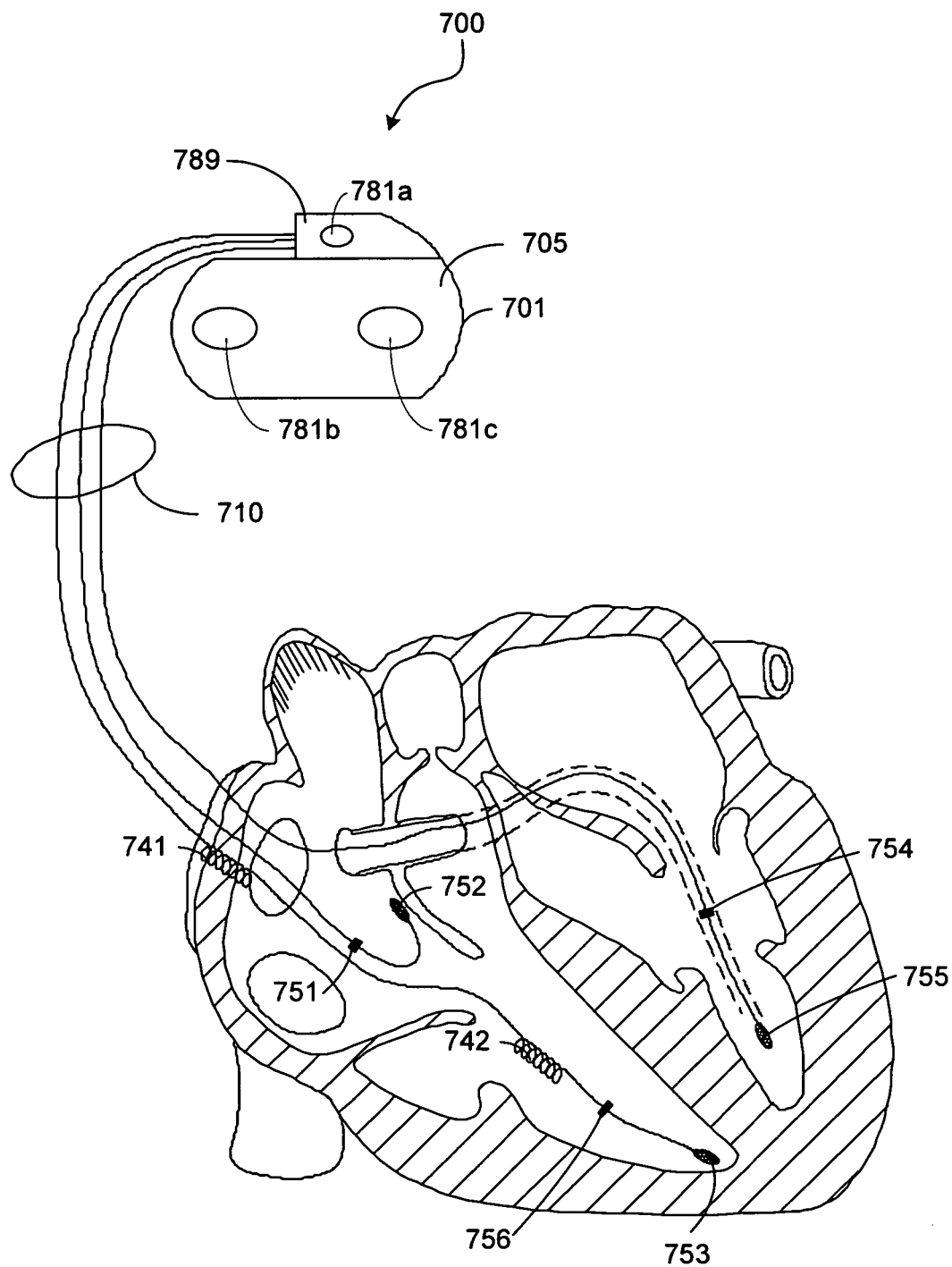
FIG. 7 illustrates a therapy device that may be used to time the delivery of cardiac pacing pulses based on local and non-local sensing in accordance with embodiments of the invention.

Referring now to FIG. 7, the implantable device illustrated in FIG. 7 is an embodiment of a therapy device 700 that may be used to time the delivery of cardiac pacing pulses based on local and non-local sensing in accordance with embodiments of the invention. In this example, the therapy device 700 includes a pulse generator 705 electrically and physically coupled to an intracardiac lead system 710.

Portions of the intracardiac lead system 710 are inserted into the patient's heart. The intracardiac lead system 710 includes one or more electrodes configured to sense electrical cardiac activity of the heart and deliver electrical stimulation to the heart. Additionally, the cardiac electrodes and/or other sensors may be used to sense the patient's transthoracic impedance, and/or sense other physiological parameters, such as cardiac chamber pressure or temperature. The electrodes shown in FIG. 7 illustrate one possible arrangement of electrodes. Many other electrode arrangements, including intracardiac and/or subcutaneous intrathoracic and non-intrathoracic electrodes, may be used to achieve local and non-local sensing and are considered to fall within the scope of the invention. The lead system 710 may include wired and/or wirelessly coupled electrodes. In wireless configurations, sensed signals from the electrodes are wirelessly communicated to the pulse generator 705 and/or may also be communicated wirelessly to a patient-external device.

Portions of the housing 701 of the pulse generator 705 may optionally serve as one or multiple can or indifferent electrodes. The housing 701 is illustrated as incorporating a header 789 that may be configured to facilitate removable attachment between one or more leads and the housing 701. The housing 701 of the pulse generator 705 may include one or more can electrodes 781b, and 781c. The header 789 of the pulse generator 705 may include one or more indifferent electrodes 781a. The housing 701 and/or header 789 may include any number of electrodes positioned anywhere in or on the housing 701 and/or header 789. In various configurations, one or more housing/header electrodes 781a-781c may be used as one electrode of an electrode pair 781a-781c providing non-local sensing and another one or more housing/header electrodes 781a-781c may be used as the other electrode of the electrode pair. In other embodiments, one or more housing/header electrodes 781a-781c may be used as one electrode of a non-local electrode pair providing non-local sensing and one or more intracardiac electrodes such as the SVC coil 741, RA ring 751, RV coil 742, RV ring 756, and/or LV ring electrode 754 may be used as the other electrode of the non-local electrode pair. Local signals may be sensed via tip electrodes configured for local sensing such as the RA tip electrode 752, the RV tip electrode 753 and the LV distal electrode 755.

Communications circuitry is disposed within the housing 701 for facilitating communication between the pulse generator 705 and a patient-external device, such as an external programmer or advanced patient management (APM) system, for example. The communications circuitry may also facilitate unidirectional or bidirectional communication with one or more implanted, external, cutaneous, or subcutaneous physiologic or non-physiologic sensors, patient-input devices and/or information systems.

The pulse generator 705 may include circuitry, such as filters, amplifiers, digitizers and/or other signal processing circuitry for useful in sensing local and non-local cardiac signals. The pulse generator may also include circuitry for detecting and/or measuring signal features. Control circuitry for controlling pacing and/or defibrillation/cardioversion therapy and other functions of the pacemaker is enclosed in the housing of the pulse generator 705.

The lead system 710 and pulse generator 705 of the therapy device 700 may incorporate one or more transthoracic impedance sensors that may be used to acquire the patient's respiratory waveform, and/or other respiratory-related information. The transthoracic impedance sensor may include, for example, one or more intracardiac electrodes 741, 742, 751-756 positioned in one or more chambers of the heart. The intracardiac electrodes 741, 742, 751-756 may be coupled to impedance drive/sense circuitry positioned within the housing 701 of the pulse generator 705. Information from the transthoracic impedance sensor and/or an activity sensor may be used to adapt the rate of pacing to correspond to the patient's activity and/or hemodyriamic need.

The lead system 710 may include one or more cardiac pace/sense electrodes 751-756 positioned in, on, or about one or more heart chambers for sensing electrical signals from the patient's heart and/or delivering pacing pulses to the heart. The intracardiac sense/pace electrodes 751-756, such as those illustrated in FIG. 7, may be used to sense and/or pace one or more chambers of the heart, including the left ventricle, the right ventricle, the left atrium and/or the right atrium. The lead system 710 may include one or more defibrillation electrodes 741, 742 for delivering defibrillation/cardioversion shocks to the heart.

The pulse generator 705 may include circuitry for detecting cardiac arrhythmias and/or for controlling pacing or defibrillation therapy in the form of electrical stimulation pulses or shocks delivered to the heart through the lead system 710.

In some embodiments, the pulse generator 705 may include circuitry for determining interchamber pacing timing intervals, such as AVD and/or IVD, using the local and non-local signals. In other embodiments, the pulse generator 705 may transfer sensed or derived information relevant to the determination of pacing timing to a patient-external device. Following download of the implantably sensed or derived information, determination of pacing timing intervals may be made by the patient-external device or may be made by a human analyst. Following pacing timing determination, the pacing timing intervals may be transferred to the therapy device 700 and used to control pacing pulses delivered to the heart to effect a pacing therapy for enhancing cardiac function.

Figure 8:
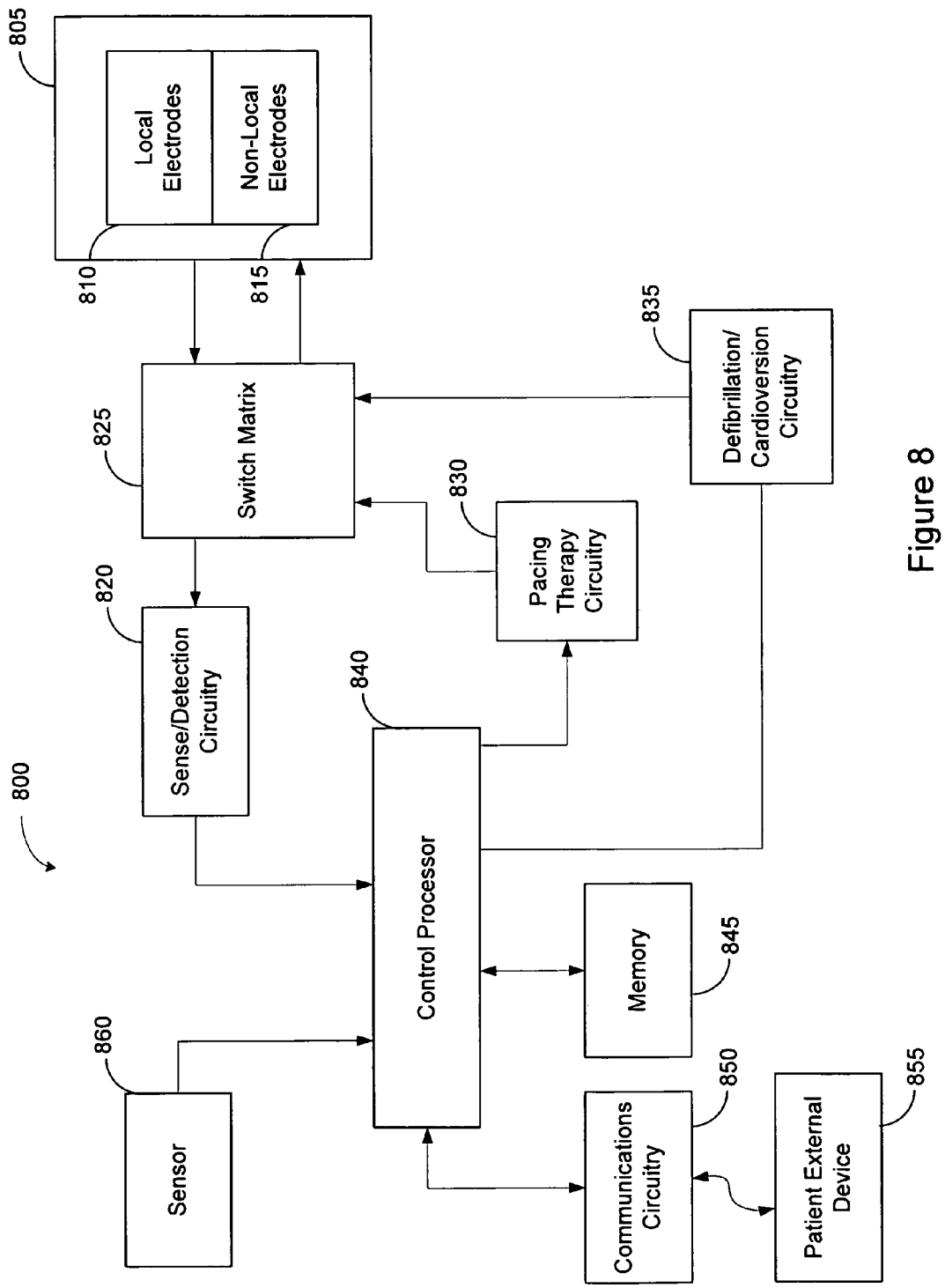
FIG. 8 is a block diagram depicting various components of a system that may be used to deliver pacing therapy with pacing timing implemented in accordance with embodiments of the invention.

FIG. 8 is a block diagram depicting various components of a system that may be used to deliver pacing therapy with pacing timing implemented in accordance with embodiments of the invention. The components, functionality, and configurations depicted are intended to provide an understanding of various features and combinations of features that may be incorporated in such a system. It is understood that a wide variety of device configurations are contemplated, ranging from relatively sophisticated to relatively simple designs. As such, particular configurations may include some components illustrated in FIG. 8, while excluding other components. In certain embodiments, the arrangement of the functional blocks may vary from the arrangement depicted.

FIG. 8 illustrates functionality for timing delivery of pacing pulses based on the use of local and non-local signals. In some embodiments, the functionality may be incorporated into an implantable device. In other embodiments, the functionality may be incorporated in the patient-external programmer. In yet other embodiments, the functionality may be divided between a patient implantable device and a patient external device.

In some implementations, the control processor 840 may execute a relatively sophisticated algorithm that automatically determines pacing the control processor may format information for display to allow a human analyst to review information from local and non-local signals to make a determination regarding optimal timing for pacing.

Illustrated in FIG. 8 is a therapy system 800 having control processor 840 coupled to appropriate memory (volatile and/or non-volatile) 845, it being understood that any logic-based control architecture may be used. The control processor 840 is also coupled to circuitry and components configured to sense electrical signals produced by the heart and to deliver electrical stimulation energy to the heart under predetermined conditions to treat cardiac arrhythmias and/or other cardiac conditions. The electrical energy delivered by the therapy device 800 may be in the form of low energy pacing pulses or high-energy pulses for cardioversion or defibrillation.

Cardiac signals are sensed using cardiac electrodes 805, including local 810 and non-local electrodes 815. A switch matrix 825 is employed to selectably couple various combinations of the cardiac electrodes 805 to the sensing circuitry 820. The sensed cardiac signals are received by sensing circuitry 820, which includes circuitry and for amplifying, filtering and/or digitizing the local and non-local signals. The sensed cardiac signals may optionally be processed by noise reduction circuitry (not shown), which may reduce noise and or increase the signal to noise ratio (SNR) of the signals before signals are sent to the control processor 840.

The control processor 840 may include arrhythmia detection circuitry such as a signal processor that coordinates analysis of the sensed cardiac signals and/or other sensor inputs to detect cardiac tachyarrhythmia. Rate based and/or morphological discrimination algorithms may be implemented by the control processor 840 to detect and verify the presence and severity of an arrhythmic episode. If arrhythmia is detected, the therapy control processor 840 may coordinate delivery of an appropriate therapy, such as anti-tachyarrhythmia pacing therapy (ATP), cardioversion, and/or defibrillation via the defibrillation/cardioversion circuitry 835 to terminate or mitigate the arrhythmia.

The therapy device 800 incorporates cardiac pacing capability in addition to, or to the exclusion of, cardioversion and/or defibrillation capabilities. As is shown in FIG. 8, the therapy device 800 includes pacing therapy circuitry 830 that is coupled to the therapy control processor 840 and to the electrodes 805 via the switch matrix 825. Under the control of control processor 840, the pacing therapy circuitry 830 delivers pacing pulses to the heart in accordance with a selected pacing therapy, such as a pacing therapy using pacing timing intervals determined by the approaches described herein.

Control signals, developed in accordance with a pacing regimen by pacemaker circuitry within the therapy control processor 840, are initiated and transmitted to the pacing therapy circuitry 830 where pacing pulses are generated. A pacing therapy, such as those discussed and incorporated herein, may be modified by the therapy control processor 840. Pacing therapy may be implemented to terminate or mitigate cardiac tachyarrhythmia, to provide a heart rate that ensures sufficient blood flow, and/or to enhance synchronization of the heart chamber contractions.

The sensing circuitry 820 is configured to sense local and non-local cardiac electrical signals via the electrodes 810, 815 and to communicate cardiac signal information to the control processor 840. The control processor 840 may also be configured to receive signals from one or more additional physiologic and/or non-physiologic sensors 860. The additional physiological signals and/or non-physiological signals may be used in connection with various diagnostic, therapeutic or monitoring implementations. For example, the therapy device 800 may include sensors or circuitry for detecting respiratory system signals, cardiac system signals, and/or signals related to patient activity or metabolic demand. The therapy control processor 840 may adapt the pacing rate based on the patient's sensed metabolic demand.

Cardiac signals sensed via the local and/or non-local electrode pairs 810, 815 are used by the control processor 840 to determine timing for pacing pulses as described herein. For example, the control processor 840 may analyze the sensed signals to detect signal features. The control processor 840 may determine interchamber timing delays, such as AVD and/or IVD, for pacing therapy based on the signal features. The control processor 840 may implement trigger pacing and may deliver backup pacing based on local and non-local sensing.

Memory circuitry 845 of the therapy device 800 contains parameters for operating in various monitoring, defibrillation, and pacing modes. The memory circuitry 845 may also be configured to store historical data, which may be used for various purposes and transmitted to an external receiving device 855 as needed or desired. For example, in certain embodiments, the memory circuitry 845 may store formulas and/or tables used in connection with determining pacing timing. The formulas and/or tables may be indexed according to heart rate.

Communications circuitry 850 is coupled to the control processor 840. The communications circuitry 850 allows communication between devices, such as patient-external devices 855 and patient-implantable devices. In one configuration, the communications circuitry 850 and the patient-external device 855 use a wire loop antenna and a radio frequency telemetric link, as is known in the art, to receive and transmit signals and data between the patient-external device 855 and communications circuitry 850. In this manner, programming commands and data may be transferred to the control processor 840 from the patient-external device 855 during and after implant. Using a patient-external programmer, a physician is able to set or modify various parameters used by the therapy control processor 850. For example, a physician may set or modify parameters affecting monitoring, detection, pacing, and defibrillation functions of the therapy control processor 840.

In certain embodiments, the control processor 840 transmits information for determination of pacing timing to the patient-external device 855. The information may include, for example, cardiac electrical signals obtained via local and/or non-local sensing, markers indicating the timing of certain features or points, measured characteristics or features of the signals, and/or other information. The patient-external device 855 may use the transmitted information to determine pacing timing intervals or may format and display information from local and non-local sensing to facilitate the determination of pacing timing intervals by a human analyst.

Processes for timing the delivery of pacing pulses based on cardiac signals obtained via local and non-local sensing in accordance with embodiments of the invention may be implemented by an implantable device, by a patient-external device, such as a programmer or advanced patient management system, or by a manually implementable procedure, such as by using a printed table lookup to compute the optimal values, and/or by any combination of these techniques.

In one embodiment, the patient-external programmer 855 communicates with the control processor 840 over a telemetry link and receives either raw electrogram data, markers corresponding to particular sensed events, and/or measurements of intervals between sensed events or feature widths as computed by the implantable device. The external programmer 855 may then compute optimal settings for pacing timing intervals which are either transmitted to the control processor 840 for immediate reprogramming or presented to a clinician operating the external programmer as recommendations.

In another embodiment, the external programmer 855 may present the data, markers, and/or measurements to a human analyst who then programs the control processor 840 in accordance with an algorithm. In yet a further embodiment, determination of the pacing timing may be fully automatic and performed by an implantable therapy device.

CRT patients who are paced using inappropriate pacing timing delays may not benefit by CRT therapy. One goal of CRT is to optimize the LA/LV timing in order to increase atrioventricular synchrony and thus enhance cardiac performance. The use of RA local signals to determine timing intervals is hindered by the lack of LA information available using RA local sensing alone. The difference in activation sequences between intrinsic and paced activity further complicates achieving optimal atrioventricular synchrony due to variable patient physiology and pathology. Non-local sensing of signals provides additional information useful for determining pacing timing that promotes atrioventricular synchrony and improved cardiac performance.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method for delivery of pacing therapy to a heart by a patient-internal medical device (PIMD) that includes a pulse generator disposed in a patient-implantable housing that may be provided with a header, the method comprising:

sensing, using body-implantable electrodes, at least one local cardiac electrical signal predominantly indicating cardiac electrical activity close to a local site within a heart chamber and at least one non-local cardiac electrical signal comprising a superposition of cardiac electrical signals occurring within the heart and associated with a cardiac contraction, the body-implantable electrodes including a non-local cardiac electrode pair that is used to sense the non-local cardiac electrical signal, the non-local cardiac electrode pair including a first electrode positioned in or on the housing or header and a second electrode positioned in or on the housing or header;

sensing for a feature of the local signal corresponding to activation of the heart chamber;

sensing for a feature of the non-local signal corresponding to the activation of the heart chamber and including information about activation of a plurality of heart chambers; and timing delivery of one or more pacing pulses based on a temporal relationship between timing of the feature of the local signal and timing of the feature of the non-local signal;

wherein the method is carried out on a beat-by-beat basis, such that the sensing for the feature of the local signal, the sensing for the feature of the non-local signal, and the timing delivery of a given one of the one or more pacing pulses are all associated with a given cardiac beat.

2. The method of claim 1, wherein sensing the at least one local cardiac electrical signal, sensing the at least one non-local cardiac electrical signal, and timing delivery of the one or more pacing pulses all occur during one cardiac cycle.

3. The method of claim 1, wherein timing delivery of the pacing pulses comprises determining an atrioventricular delay based on the temporal relationship between the local feature timing and the non-local feature timing.

4. The method of claim 1, wherein:
sensing the local cardiac signal comprises sensing from a local atrial site;
sensing for the local signal feature comprises sensing for a local P-wave;
sensing for the non-local signal feature comprises sensing for a non-local P-wave; and
timing the delivery of the pacing pulses comprises determining an atrioventricular delay based on the temporal relationship between the local P-wave and the non-local P-wave.

5. The method of claim 1, wherein:
sensing the local cardiac signal comprises sensing from a local atrial site;
sensing for the local signal feature comprises sensing for a local P-wave;
sensing for the non-local signal feature comprises sensing for a non-local P-wave; and
timing the delivery of the pacing pulses comprises:
  initiating an atrioventricular delay based on the detection of the local P-wave; and
  ending the atrioventricular delay based on the detection of the non-local P-wave.

6. A method for delivery of pacing therapy, comprising:
sensing, using body-implantable electrodes, at least one local cardiac electrical signal and at least one non-local cardiac electrical signal;
sensing for a feature of the local signal corresponding to activation of a heart chamber;
sensing for a feature of the non-local signal corresponding to activation of the heart chamber; and
timing delivery of one or more pacing pulses based on a temporal relationship between timing of the feature of the local signal and timing of the feature of the non-local signal;
wherein the body-implantable electrodes include a first electrode positioned in or on an implantable housing or header and a second electrode positioned in or on the implantable housing or header, the first and second electrodes being used for sensing for the feature of the non-local signal; and
wherein timing the delivery of the pacing pulses comprises:

triggering delivery of a pacing pulse based on the non-local feature if the non-local feature is detected; and
triggering delivery of the pacing pulse based on the local feature if the non-local feature is not detected.

7. The method of claim 6, wherein:
triggering delivery of the pacing pulse if the non-local feature is detected comprises triggering delivery of an atrial pacing pulse if a non-local P-wave is detected; and
triggering delivery of the pacing pulse comprises triggering delivery of the atrial pacing pulse based on a local P-wave.

8. The method of claim 6, wherein:
triggering delivery of the pacing pulse if the non-local feature is detected comprises triggering delivery of a ventricular pacing pulse if a non-local QRS complex is detected; and
triggering delivery of the pacing pulse based on the local feature comprises triggering delivery of the ventricular pacing pulse based on a local QRS complex if the non-local QRS complex is not detected.

9. An implantable cardiac rhythm management device, comprising:
a patient-internal medical device (PIMD) including a pulse generator disposed in a patient-implantable housing that may be provided with a header;
a plurality of implantable electrodes coupled to the housing and configured to electrically couple to a heart, at least a first pair of the plurality of electrodes configured to sense a local cardiac signal predominantly indicating cardiac electrical activity close to a local site within a heart chamber and at least a second pair of the plurality of electrodes configured to sense a non-local cardiac signal comprising a superposition of cardiac electrical signals occurring within the heart and associated with a cardiac contraction, the second pair of electrodes including a first electrode positioned in or on the housing or header and a second electrode positioned in or on the housing or header;
sense circuitry coupled to the first and second electrode pairs and configured to sense the local cardiac signal via the first electrode pair and the non-local cardiac signal via the second electrode pair;
detection circuitry configured to detect a feature of the local signal associated with activation of a heart chamber and to detect a feature of the non-local signal associated with activation of the heart chamber; and
a control processor configured to time delivery of one or more pacing pulses based on a temporal relationship between timing of the local signal feature and timing of the non-local signal feature;
wherein the device is configured to operate on a beat-by-beat basis, such that the control processor is configured to deliver a given one of the one or more pacing pulses during a same cardiac beat in which the sense circuitry senses the local cardiac signal and the non-local cardiac signal.

10. The device of claim 9, wherein:
the local signal feature comprises a local P-wave;
the non-local signal feature comprises a non-local P-wave; and
the control processor is configured determine an atrioventricular delay based on the temporal relationship between the timing of the local P-wave and the timing of the non-local P-wave, the atrioventricular delay used to time delivery of the one or more pacing pulses.

11. The device of claim 10, wherein the control processor is configured to determine the atrioventricular delay based on the temporal relationship between a beginning, end, or peak timing of the local P-wave and a beginning, end, or peak timing of the non-local P-wave.

12. The device of claim 9, wherein delivery of the pacing pulses comprises delivery of an atrioventricular synchronous pacing therapy.

13. The device of claim 9, wherein delivery of the pacing pulses comprises delivery of a bradycardia pacing therapy.

14. The device of claim 9, wherein the delivery of the pacing pulses comprises delivery of a resynchronization pacing therapy.

15. The device of claim 9, wherein:
the first pair of the plurality of electrodes is configured to sense the local cardiac signal from a local atrial site;
the detection circuitry configured to detect the local signal feature is configured to detect a local P-wave;
the detection circuitry configured to detect the non-local signal feature is configured to detect a non-local P-wave; and
the control processor configured to time delivery of the one or more pacing pulses is configured to initiate an atrioventricular delay based on the detection of the local P-wave, and to end the atrioventricular delay based on the detection of the non-local P-wave.

16. An implantable cardiac rhythm management device, comprising:
a plurality of implantable electrodes configured to electrically couple to a heart, the plurality of implantable electrodes including at least a first pair of electrodes and a second pair of electrodes;
sense circuitry coupled to the first and second electrode pairs and configured to sense a local cardiac signal via the first electrode pair and a non-local cardiac signal via the second electrode pair;
detection circuitry configured to detect a feature of the local signal associated with activation of a heart chamber and to detect a feature of the non-local signal associated with activation of the heart chamber; and
a control processor configured to time delivery of one or more pacing pulses based on a temporal relationship between timing of the local signal feature and timing of the non-local signal feature;
wherein the control processor is configured to trigger pacing based on the timing of the non-local signal feature if the non-local signal feature is detected and to trigger pacing based on the timing of the local signal feature if the non-local signal feature is not detected.

17. The device of claim 16, wherein the non-local signal feature comprises a non-local P-wave, and the local signal feature comprises a local P-wave.

18. The device of claim 16, wherein the non-local signal feature comprises a non-local QRS complex, and the local signal feature comprises a local QRS complex.

19. A system for delivery of pacing therapy to a heart, comprising:
a patient-internal medical device (PIMD) including a pulse generator disposed in a patient-implantable housing that may be provided with a header;
a first pair of body-implantable electrodes coupled to the housing and configured to sense a local cardiac signal predominantly indicating cardiac electrical activity close to a local site within a heart chamber;
a second pair of body-implantable electrodes coupled to the housing and configured to sense a non-local cardiac signal comprising a superposition of cardiac electrical signals occurring within the heart and associated with a cardiac contraction, the second pair of electrodes including a first electrode positioned in or on the housing or header and a second electrode positioned in or on the housing or header;
means for detecting a feature of the local signal related to activation of a cardiac chamber;
means for detecting a feature of the non-local signal related to activation of the cardiac chamber and including information about activation of a plurality of heart chambers; and
means for timing delivery of one or more pacing pulses based on a temporal relationship between timing of the local feature and timing of the non-local feature;
wherein the device is configured to operate on a beat-by-beat basis, such that the timing means is configured to deliver a given one of the one or more pacing pulses during a same cardiac beat in which the first and second pairs of body-implantable electrodes sense the local and non-local cardiac signals respectively.

20. The system of claim 19, further comprising means for determining an atrioventricular delay based on the temporal relationship.

21. The system of claim 19, further comprising means for implementing triggered pacing based on the temporal relationship between the timing of the local signal feature and the timing of the non-local signal feature.

* * * * *